United States Patent [19]

Bovy et al.

[11] Patent Number: 5,239,113
[45] Date of Patent: Aug. 24, 1993

[54] SUBSTITUTED β-AMINO ACID DERIVATIVES USEFUL AS PLATELET AGGREGATION INHIBITORS AND INTERMEDIATES THEREOF

[75] Inventors: Phillipe R. Bovy, Ballwin; Joseph G. Rico, Manchester; Thomas E. Rogers, Ballwin; Foe S. Tjoeng, Manchester, all of Mo.; Jeffery A. Zablocki, Skokie, Ill.

[73] Assignees: Monsanto Company, St. Louis, Mo.; G. D. Searle & Co., Skokie, Ill.

[21] Appl. No.: 866,933

[22] Filed: Apr. 10, 1992

Related U.S. Application Data

[63] Continuation-in-part of Ser. No. 777,811, Oct. 15, 1991, abandoned.

[51] Int. Cl.$^5$ ............... C07C 251/24; C07C 257/18
[52] U.S. Cl. ................... 562/440; 560/13; 560/35; 562/430
[58] Field of Search ............ 560/35, 13; 562/440, 562/430; 558/414

[56]  References Cited

U.S. PATENT DOCUMENTS

| 3,862,228 | 1/1975 | Rodriguez et al. | 560/13 |
| 4,517,686 | 5/1985 | Ruoslahti et al. | 623/11 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,683,291 | 7/1987 | Zimmerman et al. | 530/324 |
| 4,857,508 | 8/1989 | Adams et al. | 514/18 |
| 4,879,313 | 11/1989 | Tjoeng et al. | 514/616 |
| 5,053,393 | 10/1991 | Tjoeng et al. | 514/18 |
| 5,084,466 | 1/1992 | Alig et al. | 514/353 |

FOREIGN PATENT DOCUMENTS

| 298820 | 6/1987 | European Pat. Off. . |
| 275748 | 7/1988 | European Pat. Off. . |
| 372486 | 10/1989 | European Pat. Off. . |
| 445796 | 3/1990 | European Pat. Off. . |

OTHER PUBLICATIONS

Koczewiak et al., Biochem. 23, 1767-1774 (1984).
Plow et al., Proc. Natl. Adac. Sci. 82, 8057-8061 (1985).
Ruggeri et al., Proc. Natl. Acad. Sci. 83, 5708-5712 (1986).
Haverstick et al., Blood 66 (4) 948-952 (1985).
Ruoslahti an Pierschbacher, Science 238, 491-497 (1987).
R. T. Boere et al, J. Organomet. Chem. 331, 161-167 (1987).
W. E. Parham, C. K. Bradsher, Acct. Chem. Res. 300 (1982).
M. Taddei and A. Ricci, Synthesis 633-635 (1986).
Ginsberg et al, J. Biol. Chem. 260 (7), 3931-3936 (1985).
C. F. Allen and J. W. Gates, Org. Synth. Coll. vol. 3 140 (1955).

Primary Examiner—José G. Dees
Assistant Examiner—B. Frazier
Attorney, Agent, or Firm—Dennis A. Bennett

[57] ABSTRACT

Novel substituted β amino acid derivatives are provided which inhibit platelet aggregation and intermediates thereof. This invention also pertains to pharmaceutical compositions and methods of using such derivatives.

2 Claims, No Drawings

SUBSTITUTED β-AMINO ACID DERIVATIVES USEFUL AS PLATELET AGGREGATION INHIBITORS AND INTERMEDIATES THEREOF

This application is a continuation-in-part of application Ser. No. 07/777,811, filed Oct. 15, 1991, now abandoned.

BACKGROUND OF THE INVENTION

1. Field of the Invention

This invention pertains to substituted β amino acid derivatives which inhibit platelet aggregation.

2. Related Art

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb-/IIIa; this is an important feature of the platelet function. Inhibitors of this interaction are useful in modulating or preventing platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. (See U.S. Pat. Nos. 4,517,686; 4,589,881; and 4,661,111). Certain relatively short peptide fragments from the same molecule were found to promote cell attachment to a substrate when immobilized on the substrate or to inhibit attachment when in a solubilized or suspended form. (See U.S. Pat. Nos. 4,578,079 and 4,614,517).

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in EP Patent Applications 275,748 and 298,820.

U.S. Pat. No. 4,879,313 discloses compounds useful as inhibitors of platelet aggregation having the formula

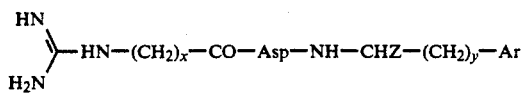

wherein
x = 6 to 10,
y = 0 to 4,
Z = H, COOH, CONH2 or C1-6 alkyl,
Ar = phenyl, biphenyl or naphthyl, each substituted with 1 to 3 methoxy groups, or an unsubstituted phenyl, biphenyl, naphthyl, pyridyl or thienyl group, and
Asp = aspartic acid residue.

European Patent Application 372,486 discloses N-acyl β amino acid derivatives of the formula:

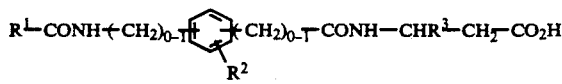

and their salts. Said compounds are useful for inhibiting platelet aggregation in the treatment of thrombosis, stroke, myocardial infarction, inflammation and arteriosclerosis, and for inhibiting metastasis.

European Patent Application 381,033 discloses amidino or guanidinoaryl substituted alkanoic acid derivatives useful for the treatment of thrombosis, apoplexy, cardiac infarction, inflammation, arteriosclerosis and tumors.

European Patent Application 445,796 discloses Acetic Acid derivatives useful as a ligand for adhesive proteins on blood platelet. As such these compounds are useful to modulate and/or inhibit platelet aggregation.

SUMMARY OF THE INVENTION

In accordance with the present invention novel substituted β amino acid derivatives are provided which modulate and/or inhibit platelet aggregation. These novel inhibitor compounds can be represented by the following chemical formula.

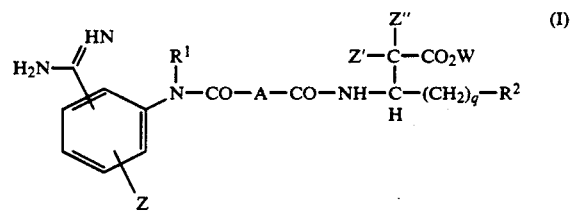

wherein
$R^1$ is selected from the group consisting of hydrogen, lower alkyl radicals, lower alkenyl radicals, aromatic hydrocarbon radicals, alicyclic hydrocarbon radicals, benzyl radicals, phenethyl radicals, wherein said radicals are optionally substituted with halogen, lower alkoxy, hydroxy and lower alkyl;

$R^2$ is selected from the group consisting of hydrogen, lower alkyl radicals, lower alkenyl radicals, lower alkynyl radicals, alicyclic hydrocarbon radicals, aromatic hydrocarbon radicals, wherein all of said radicals are optionally substituted with hydroxy, lower alkoxy, lower alkyl, halogen, nitro, cyano, azido, trialkylsilyl, ureido, ureylene, carboxyl or carbonyl derivatives, trifluoromethyl, acyloxy, alkylthio, arylthio, alkylsulfenyl, arylsulfenyl, alkylsulfonyl, arylsulfonyl, amino, alkylamino, sulfonylamino, dialkylamino, alkanoylamino, aroylamino, and phenyl and naphthyl which are optionally substituted with one or more of the following: halogen, nitro, lower alkoxy, and lower alkyl.

A is selected from the group consisting of lower alkyl radicals, lower alkenyl radicals, lower alkynyl radicals, and alicyclic radicals, wherein said radicals are optionally substituted with hydroxyl, lower alkoxy, lower alkyl, halogen, alkoxycarbonylalkyl, amino, alkylamino, dialkylamino, alkylthio, sulfonyl, and aromatic hydrocarbons which are optionally substituted with halogen, nitro, lower alkoxy and lower alkyl;

W is selected from the group consisting of hydrogen, lower alkyl radicals, lower alkenyl radicals, lower alkynyl radicals, alicyclic hydrocarbon radicals and aromatic hydrocarbon radicals, wherein said radicals are optionally substituted with hydroxyl, lower alkoxy, lower alkyl, halogen, nitro, amino, acyloxy, and phenyl and naphthyl which may be optionally substituted with halogen, nitro, lower alkoxy, and lower alkyl;

Z, Z', Z'' are independently selected from the group consisting of hydrogen, lower alkyl radicals, halogen, alkoxy, cyano, sulfonyl, carboxyl, alkoxycarbonyl, and hydroxyl radicals;

q is an integer from 0 to about 6; and with the proviso that when A is trimethylene and q is 0 then $R_2$ is not hydrogen, methyl radical or phenyl radical and also that when A is trimethylene and q is 1 then $R_2$ is not hydrogen.

$R^1$ is preferably hydrogen and benzyl radicals, $R^1$ is more preferably hydrogen.

$R^2$ is preferably lower alkenyl and lower alkynyl.

$R^2$ is more preferably vinyl, ethynyl, phenylsulfonyl or methoxycarbonyl.

A is preferably lower alkyl which may be substituted as defined above.

A is more preferably methylene, ethylene, propylene, cyclopropylene; most preferably A is ethylene or cyclopropylene; even most preferably A is ethylene.

W is preferably hydrogen or lower alkyl radicals; more preferably W is hydrogen or ethyl.

Z, Z', Z'' are preferably independently selected from the group consisting of hydrogen, chloro, benzyl, methyl, ethyl, hydroxyl, methoxy; more preferably, Z, Z', Z'' are selected from hydrogen, benzyl, ethyl; most preferable, Z, Z', Z'' are hydrogen.

q is preferably an integer of 0 to about 4; more preferably 0 to about 2; most preferably 0 or 1. Most preferred 0.

The following compounds are preferred;
Dimethyl 3-[[4-[[4-(aminoimino-methyl)phenyl]-amino]-1,4-dioxobutyl]amino]pentanedioate;
3-[[4-[[4-(aminoiminomethyl)phenyl]-amino]-1,4-dioxobutyl]amino]pentanedioic acid, monomethylester;
3-[[4-[[4-(aminoiminomethyl)phenyl]amino]-1,4-dioxobutyl]amino]pentanedioic acid;
(±)-Ethyl-3-[[4-[[4-(aminoiminomethyl)phenyl]-amino]-1,4-dioxobutyl]amino]-4-phenylsulfonyl butanoate.
(±)-3-[[4-[[4-(aminoiminomethyl)phenyl]-amino]-1,4-dioxobutyl]amino]-4-phenylsulfonyl butanoic acid;
Ethyl 3-[[4-[[4-(aminoiminomethyl)phenyl]amino)-1,4-dioxobutyl]amino]-4-pentenoate;
3-[[4-[[4-(aminoiminomethyl)phenyl]amino]-1,4-dioxobutyl]amino]4-pentenoic acid;
Ethyl 3-[[4-[[4-(aminoiminomethyl)phenyl]amino]-1,4-dioxobutyl]amino]-4-pentynoate;
(±)-3-[[4-[[4-(aminoiminomethyl)phenyl]amino]-1,4-dioxobutyl]amino]-4-pentynoic acid.

The most preferred compounds are;

Ethyl 3-[[4-[[4-(aminoiminomethyl)phenyl]amino)-1,4-dioxobutyl]amino]-4-pentenoate;
3-[[4-[[4-(aminoiminomethyl)phenyl]amino]-1,4-dioxobutyl]amino]4-pentenoic acid;
Ethyl 3-[[4-[[4-(aminoiminomethyl)phenyl]amino]-1,4-dioxobutyl]amino]-4-pentynoate;
(±)-3-[[4-[[4-(aminoiminomethyl)phenyl]amino]-1,4-dioxobutyl]amino]-4-pentynoic acid.

It is another object of the invention to provide a novel pharmaceutical composition comprising compounds of the formula I useful in inhibiting or modulating platelet aggregation or the like, particularly in inhibiting or modulating platelet aggregation by administrating an amount between 0.5 mg/kg to 10 mg/kg preferably 3 mg/kg to an animal in need thereof.

It is still another object of the invention to provide a method to therapeutically inhibit or modulate platelet aggregation or the like in a mammal in need of such treatment comprising a compound of the formula I in unit dosage form.

Many other objects and purposes of the invention will be clear from the following detailed description of the invention.

DETAILED DESCRIPTION OF THE INVENTION

A preferred embodiment of the present invention is a compound of the formula I:

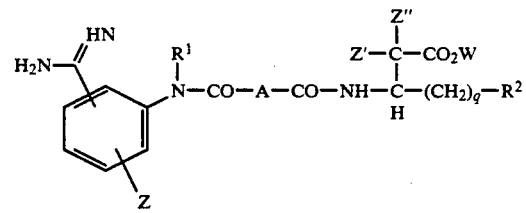

pharmaceutically acceptable salt, or prodrug thereof, wherein $R_1$ is selected from hydrogen, lower alkyl radicals of 1 to about 6 carbon atoms, lower alkenyl radicals of 1 to about 6 carbon atoms, aromatic hydrocarbon radicals, alicyclic hydrocarbon radicals of 3 to about 6 carbon atoms, benzyl radicals, phenethyl radicals, wherein said radicals are optionally substituted with halogen, lower alkoxy, hydroxy and lower alkyl;

$R_2$ is selected from hydrogen, lower alkyl radicals of 1 to about 6 carbon atoms, lower alkenyl radicals of 2 to about 6 carbon atoms, lower alkynyl radicals of 2 to about 8 carbon atoms, alicyclic hydrocarbon radicals of 3 to 6 carbon atoms, aromatic hydrocarbon radicals, wherein said radicals are optionally substituted with hydroxyl, lower alkoxy, lower alkyl, halogen, nitro, cyano, azido,ureido, ureylene, amino, trifluoromethyl, acetoxy, acetylamino, benzoylamino, carbonyl, carboxyl derivatives, alkylsulfonyl, phenylsulfonyl;

A is selected from lower alkyl radicals of 1 to about 6 carbon atoms, lower alkenyl radicals of 2 to about 6 carbon atoms, lower alkynyl radicals of 2 to about 4 carbon atoms, and alicyclic hydrocarbon radicals of 3 to about 5 carbon atoms, wherein said radicals are optionally substituted with hydroxyl, lower alkoxy, halogen, alkylthio and amino;

W is selected from hydrogen, lower alkyl radicals of 1 to about 6 carbon atoms, lower alkenyl radicals of 2 to about 6 carbon atoms, alicyclic hydrocarbon radicals of 3 to about 6 carbon atoms, and aromatic hydrocarbon radicals of 6 to about 12 carbon atoms, wherein said radicals are optionally substituted with hydroxyl, lower alkoxy, lower alkyl, halogen, nitro, amino, and acyloxy;

Z, Z', Z" are independently selected from the group consisting of hydrogen, halogen, alkoxy, cyano, sulfonyl, carboxyl, alkoxycarbonylalkyl, alkoxycarbonyl and lower alkyl radicals; and q is an integer from 0 to about 6.

$R^1$ is preferable hydrogen:

$R^2$ is preferable hydrogen lower alkyl radicals of 1 to about 6 carbon atoms and is optionally substituted as defined above. $R^2$ is more preferably hydrogen and lower alkyl.

A is preferably lower alkyl of 1 to about 6 carbon atoms which is optionally substituted as defined above. A is more preferably lower alkyl of 1 to above 6 carbon atoms.

Z is preferably hydrogen, halogen and lower alkyl, more preferably Z' is hydrogen Z' and Z" are preferably independently selected from hydrogen, lower alkyl and hydroxy.

Another preferred embodiment of the present invention is a compound of the formula I or a pharmaceutically acceptable salt or prodrug thereof,
wherein $R_1$ is selected from hydrogen, lower alkyl radicals, lower alkenyl radicals, aromatic hydrocarbon radicals, alicyclic hydrocarbon radicals, benzyl radicals, phenethyl radicals, wherein said radicals are optionally substituted with halogen, lower alkoxy, hydroxy and lower alkyl;

$R^2$ is selected from hydrogen, lower alkyl radicals, lower cycloalkyl radicals, lower alkenyl radicals, lower alkynyl radicals, phenol radicals, phenyl radicals, naphthyl radicals wherein each radical may have one or more substituents selected from the group consisting of halogen, lower alkyl, lower alkoxy, carboxyl derivatives, nitro, cyano, azido, ureido, ureylene, alkylcarbonyloxy, hydroxyl, alkylamino, dialkylamino, sulfonylamino, alkoxycarbonyl, trialkylsilyl, alkoxyimino, alkylsulfonyl, phenylsulfonyl and amino;

A is selected form lower alkyl radicals, lower cycloalkyl, alkoxycarbonylmethyl and lower alkenyl radicals wherein said radicals are optionally substituted with lower alkyl radicals;

W is selected from the group consisting of hydrogen and lower alkyl radicals;

Z, Z', Z" are independently selected from the group consisting of halogen, hydrogen, lower alkoxy, and alkoxycarbonyl, and lower alkyl radical;

Q is an integer from 0 to about 6.

$R^1$ is preferably hydrogen, lower alkyl, benzyl and phenyl. More preferably $R^1$ is hydrogen $R^2$ is preferably lower alkyl and may be optionally substituted as defined above A is preferably lower alkyl and lower cycloalkyl. A is more preferably lower cycloalkyl.

Z is preferably hydrogen, halogen and lower alkyl.

Z' and Z" are preferably independently selected from hydrogen, lower alkyl and hydroxy.

Q is preferably 0 to about 4, more preferably 0 to about 2, most preferably 1.

It is contemplated that the following compounds should be exemplifying examples:

methyl-D,L-b-[[4-[[4-(aminoiminomethyl)phenyl]amino]-1,4-dioxobutyl]amino]-3-butanoate;

isopropyl-D,L-b-[[4-[[4-(aminoiminomethyl)phenyl]amino]-1,4-dioxobutyl]amino]-3-butanoate;

cyclopropyl-D,L-b-[[4-[[4-(aminoiminomethyl)phenyl]amino]-1,4-dioxobutyl]amino]-3-butanoate;

hexyl-D,L-b-[[4-[[4-(aminoiminomethyl)phenyl]amino]-1,4-dioxobutyl]amino]-3-butanoate;

D,L-3-[[4-[[4-(aminoiminomethyl)phenyl]N-methylamino]-1,4-dioxobutyl]amino]-3-phenylpropionic acid;

D,L-3-[[4-[[4-(aminoiminomethyl)phenyl]N-methylamino]-1,4-dioxobutynyl]amino]-3-phenylpropionic acid;

D,L-3-[[4-[[4-(aminoiminomethyl)phenyl]N-phenylamino]-1,4-dioxobutyl]amino]-3-phenylpropionic acid;

D,L-3-[[4-[[3-methyl-4-(aminoiminomethyl)phenyl]amino]-1,4-dioxobutyl]amino]-3-phenylpropionic acid;

D,L-3-[[4-[[2-fluoro-4-(aminoiminomethyl)phenyl]amino]-1,4-dioxobutyl]amino]-3-phenylpropionic acid;

D,L-3-[[4-[[2,6-difluoro-4-(aminoiminomethyl)phenyl]amino]-1,4-dioxobutyl]amino]-3-phenylpropionic acid;

D,L-3-[[4-[[4-(aminoiminomethyl)naphthyl]amino]-1,4-dioxobutyl]amino]-3-phenylpropionic acid;

D,L-3-[[4-[[4-(aminoiminomethyl)phenyl]amino]-1,4-dioxo-2,2,3,3-tetrafluoro-butyl]amino]-3-phenylpropionic acid;

ethyl-D,L-3-[[4-[[4-(aminoiminomethyl)phenyl]N-methyl-amino]-1,4-dioxobutyl]amino]-3-phenylpropanoate;

ethyl-D,L-3-[[4-[[4-(aminoiminomethyl)phenyl]N-phenyl-amino]-1,4-dioxobutynyl]amino]-3-phenylpropanoate;

ethyl-D,L-3-[[4-[[4-(aminoiminomethyl)phenyl]N-phenyl-amino]-1,4-dioxobutyl]amino]-3-phenylpropanoate;

ethyl-D,L-3-[[4-[[3-methyl-4-(aminoiminomethyl)phenyl]amino]-1,4-dioxobutyl]amino]-3-phenylpropanoate;

ethyl-D,L-3-[[4-[[2-fluoro-4-(aminoiminomethyl)phenyl]amino]-1,4-dioxobutyl]amino]-3-phenylpropanoate;

ethyl-D,L-3-[[4-[[2,6-difluoro-4-(aminoiminomethyl)phenyl]amino]-1,4-dioxobutyl]amino]-3-phenylpropanoate;

ethyl-D,L-3-[[4-[[4-(aminoiminomethyl)naphthyl]amino]-1,4-dioxobutyl]amino]-3-phenylpropanoate;

ethyl-D,L-3-[[4-[[4-(aminoiminomethyl)phenyl]amino]-1,4-dioxo-2,2,3,3-tetrafluoro-butyl]amino]-3-phenylpropanoate;

ethyl-D,L-b-[[4-[[4-(aminoiminomethyl)phenyl]N-methyl-amino]-1,4-dioxobutyl]amino]-3-butanoate;

ethyl-D,L-b-[[4-[[4-(aminoiminomethyl)phenyl]N-phenyl-amino]-1,4-dioxobutynyl]amino]-3-butanoate;

ethyl-D,L-b-[[4-[[4-(aminoiminomethyl)phenyl]N-phenyl-amino]-1,4-dioxobutyl]amino]-3-butanoate;

ethyl-D,L-b-[[4-[[3-methyl-4-(aminoiminomethyl)phenyl]amino]-1,4-dioxobutyl]amino]-3-butanoate;

ethyl-D,L-b-[[4-[[2-fluoro-4-(aminoiminomethyl)-phenyl]amino]-1,4-dioxobutyl]amino]-3-butanoate;
ethyl-D,L-b-[[4-[[2,6-difluoro-4-(aminoiminomethyl)-phenyl]amino]-1,4-dioxobutyl]amino]-3-butanoate;
ethyl-D,L-b-[[4-[[4-(aminoiminomethyl)naphthyl]amino]-1,4-dioxobutyl]amino]-3-butanoate;
D,L-3-[[4-[[4-(aminoiminomethyl)phenyl]N-methyl-amino]-1,4-dioxobutyl]amino]-3-phenylpropionic acid;
D,L-3-[[4-[[4-(aminoiminomethyl)phenyl]N-methyl-amino]-1,4-dioxobutyl]amino]-3-phenylpropionic acid;
D,L-3-[[4-[[4-(aminoiminomethyl)phenyl]N-phenyl-amino]-1,4-dioxobutyl]amino]-3-phenylpropionic acid;
D,L-3-[[4-[[3-methyl-4-(aminoiminomethyl)phenyl-]amino]-1,4-dioxobutyl]amino]-3-phenylpropionic acid;
D,L-3-[[4-[[2-fluoro-4-(aminoiminomethyl)phenyl-]amino]-1,4-dioxobutyl]amino]-3-phenylpropionic acid;
D,L-3-[[4-[[2,6-difluoro-4-(aminoiminomethyl)phenyl-]amino]-1,4-dioxobutyl]amino]-3-phenylpropionic acid;
D,L-3-[[4-[[4-(aminoiminomethyl)naphthyl]amino]-1,4-dioxobutyl]amino]-3-phenylpropionic acid;
D,L-3-[[4-[[4-(aminoiminomethyl)phenyl]amino]-1,4-dioxo-2,2,3,3-tetrafluoro-butyl]amino]-3-phenylpropionic acid;
ethyl-D,L-3-[[4-[[4-(aminoiminomethyl)phenyl]N-methyl-amino]-1,4-dioxobutyl]amino]-3-phenyl-propanoate;
ethyl-D,L-3-[[4-[[4-(aminoiminomethyl)phenyl]N-phenyl-amino]-1,4-dioxobutynyl]amino]-3-phenyl-propanoate;
ethyl-D,L-3-[[4-[[4-(aminoiminomethyl)phenyl]N-phenyl-amino]-1,4-dioxobutyl]amino]-3-phenylpropanoate;
ethyl-D,L-3-[[4-[[3-methyl-4-(aminoiminomethyl)-phenyl]amino]-1,4-dioxobutyl]amino]-3-phenyl-propanoate;
ethyl-D,L-3-[[4-[[2-fluoro-4-(aminoiminomethyl)-phenyl]amino]-1,4-dioxobutyl]amino]-3-phenyl-propanoate;
ethyl-D,L-3-[[4-[[2,6-difluoro-4-(aminoiminomethyl)-phenyl]amino]-1,4-dioxobutyl]amino]-3-phenyl-propanoate;
ethyl-D,L-3-[[4-[[4-(aminoiminomethyl)naphthyl]amino]-1,4-dioxobutyl]amino]-3-phenylpropanoate;
ethyl-D,L-3-[[4-[[4-(aminoiminomethyl)phenyl]amino]-1,4-dioxo-2,2,3,3-tetrafluoro-butyl]amino]-3-phenyl-propanoate;
3-[[[2-[[[4-(aminoiminomethyl)phenyl]amino]carbonyl]-cyclopropyl]carbonyl]amino]-3-phenylpropionic acid;
3-[[[2-[[[4-(aminoiminomethyl)phenyl]amino]carbonyl]-cyclobutyl]carbonyl]amino]-3-phenylpropionic acid;
3-[[[2-[[[4-(aminoiminomethyl)phenyl]amino]carbonyl]-cyclopentyl]carbonyl]amino]-3-phenylpropionic acid;
3-[[[2-[[[4-(aminoiminomethyl)phenyl]amino]carbonyl]-cyclohexyl]carbonyl]amino]-3-phenylpropionic acid;
ethyl-3-[[[2-[[[4-(aminoiminomethyl)phenyl]amino]car-bonyl]cyclopropyl]carbonyl]amino]-3-phenyl-propanoate;
ethyl-3-[[[2-[[[4-(aminoiminomethyl)phenyl]amino]car-bonyl]cyclobutyl]carbonyl]amino]-3-phenylpropano-ate;
ethyl-3-[[[2-[[[4-(aminoiminomethyl)phenyl]amino]car-bonyl]cyclopentyl]carbonyl]amino]-3-phenyl-propanoate and;
ethyl-3-[[[2-[[[4-(aminoiminomethyl)phenyl]amino]car-bonyl]cyclohexyl]carbonyl]amino]-3-phenyl-propanoate.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl,ethyl, n-pro-pyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, pentenyl-1, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radicals in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethyl-butyn-1-yl radicals and the like.

The term "alicyclic hydrocarbon" or "cycloalkyl" means a aliphatic radical in a ring with 3 to about 10 carbon atoms, and preferably from 3 to about 6 carbon atoms. Examples of suitable alicyclic radicals include cyclopropyl, cyclopropylenyl,cyclobutyl, cyclopentyl, cyclohexyl,2-cyclohexen-1-ylenyl, cyclohexenyl and the like.

The term "aromatic hydrocarbon radical" means 4 to about 16 carbon atoms,preferably 6 to about 12 carbon atoms,more preferably 6 to about 10 carbon atoms. Examples of suitable aromatic hydrocarbon radicals include phenyl,naphthyl, and the like The term "acyloxy" encompasses acyl from 1 to about 8 carbon atoms. Suitable examples include al-kanoyloxy, benzoyloxy and the like.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopro-poxy, n-butoxy, iso-butoxy, sec-butoxy, tert-butoxy and the like.

The term "carboxyl derivatives" refers to a carbox-ylic acid derivative, such as the following:
1. ester (COOR)

Wherein R can be hydrogen, alicyclic hydrocarbon radical or aromatic hydrocarbon radical,
2. amide (CONR'R")

Wherein R' and R" are independently selected from the group consisting of hydrogen, linear or alicyclic hydrocarbon, aromatic hydrocarbon radical, hydroxy or alkoxy radical, The term "carbonyl derivative" is defined as:

R is as defined above. X can be oxygen, sulfur or N—R' wherein R' is defined as above. The term halogen means fluorine, chlorine, bromine or iodine.

The term "pharmaceutically acceptable salt" refers to a salt prepared by contacting a compound of formula (I), with an acid whose anion is generally considered suitable for human consumption. Examples of pharmacologically acceptable salts include the hydrochloride, hydrobromide, hydroiodide, sulfate, phosphate, acetate, propionate, lactate, maleate, oxalate, malate, succinate, and tartrate and citrate salts. All of these salts may be prepared by conventional means by reacting, for example, the appropriate acid with the corresponding compound of Formula I.

Suitable pharmaceutically-acceptable base addition salts of compounds of Formula I,II and III, include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine.

The term "prodrug" refers to a compound that is made more active in vivo.

Total daily dose administered to a host in single or divided doses may be in amounts, for example, from 0.001 to 100 mg/kg body weight daily and more usually 0.01 to 10 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diets, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable.

Suppositories for rectal administration of the drug can be prepared by mixing the drug with a suitable nonirritating excipient such as cocoa butter and polyethylene glycols which are solid at ordinary temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more active pharmaceutical agents. When administered as a combination, the therapeutic agents can be formulated as separate compositions which are given at the same time or different times, or the therapeutic agents can be given as a single composition.

In the structures and formulas herein, the bond drawn across a bond of an aromatic ring can be to any available atom on the aromatic ring.

The compounds in this invention can exist in various isomeric forms and all such isomeric forms are meant to be included. Tautomeric forms are also included in the invention. Pharmaceutically acceptable salts of such isomers and tautomers are meant to be included as well.

It is also contemplated that Beta amino acids ($H_2N$—$CHR$—$CH_2$—$CO_2H$) used in this invention may be replaced by Homo Beta amino acids ($H_2N$—$CH_2$—$CHR$—$CO_2H$).

The compounds listed above may be prepared by standard synthetic methods combined with methods analogous to solution phase peptide synthesis [see: The Peptides: Analysis, Synthesis, Biology (E. Gross and J. Meienhofer, eds.), Vol. 1–5, Academic Press, New York)], the disclosure of which is hereby incorporated by reference.

Five general synthetic sequences are outlined in Schemes 1–5.

SCHEME I

In Scheme I. The aminobenzamidine 1 (i.e., Z is hydrogen) is coupled to an alkanoic, alkenoic (both substituted or not) or alkynoic diacid. An activated form of the diacid is preferentially used. These activated forms include anhydrides, internal anhydride, acid chloride or one of the various activated forms as described in *Principles of Peptide Synthesis*, Bodansky, 1984, Springer-Verlag, the disclosure of which is hereby incorporated by reference. A highly preferred procedure involves condensation of an anhydride (e.g., succinic anhydride 2) with a salt of aminobenzamidine 1. The reaction is best conducted in a polar solvent such as methylene chloride, acetonitrile, dioxane, dimethylformamide, dimethylsulfoxide or a mixture of such solvents in the presence of an acid binding agent such as sodium, potassium or cesium carbonate, triethylamine, pyridine, sodium hydride, dimethylaminopyridine, diazabicycloundecene, or a mixture of such agents, at temperatures ranging between 0° C. and 120° C. The final compounds are obtained by coupling of the amidine derivative 3 with a properly protected β-aminoacid. The amide bonds are formed using standard coupling reagents, e.g., dicyclohexylcarbodiimide (DCC), carbonyldiimidazole, disuccinimidyl carbonate (DSC), benzotriazole-1-yl-oxytris-(dimethylamino)-phosphonium hexafluorophosphate (BOP) or isobutyl chloroformate (mixed anhydride method). When the β-amino acid used in the coupling was protected as an ester of the carboxylic acid function (4, W=alkyl, aryl, ...), the free acids 5 are obtained by a suitable deprotection method as described by T. H. Greene in "Protective Group in Organic Synthesis", Wiley-Interscience, 1980, the disclosure of which is hereby incorporated by reference.

($H_2S$) followed by alkylation with methyl iodide. Next, treatment of the thioimidate with ammonium acetate affords the amidine as the salt (HI). Alternatively, the nitrile 7 can be converted to the amidine 8 by the use of lithium bis(trimethylsilyl)amide in an inert solvent such as diethyl ether (R. T. Boere et al., *J. Organomet. Chem.*, 331, 161-67, 1987), the disclosure of which is hereby incorporated by reference. The desired compounds are obtained by coupling of the amidine derivative 8 with a properly functionalized β-aminoacid. The amide bonds are formed using standard coupling reagents as described above for Scheme I.

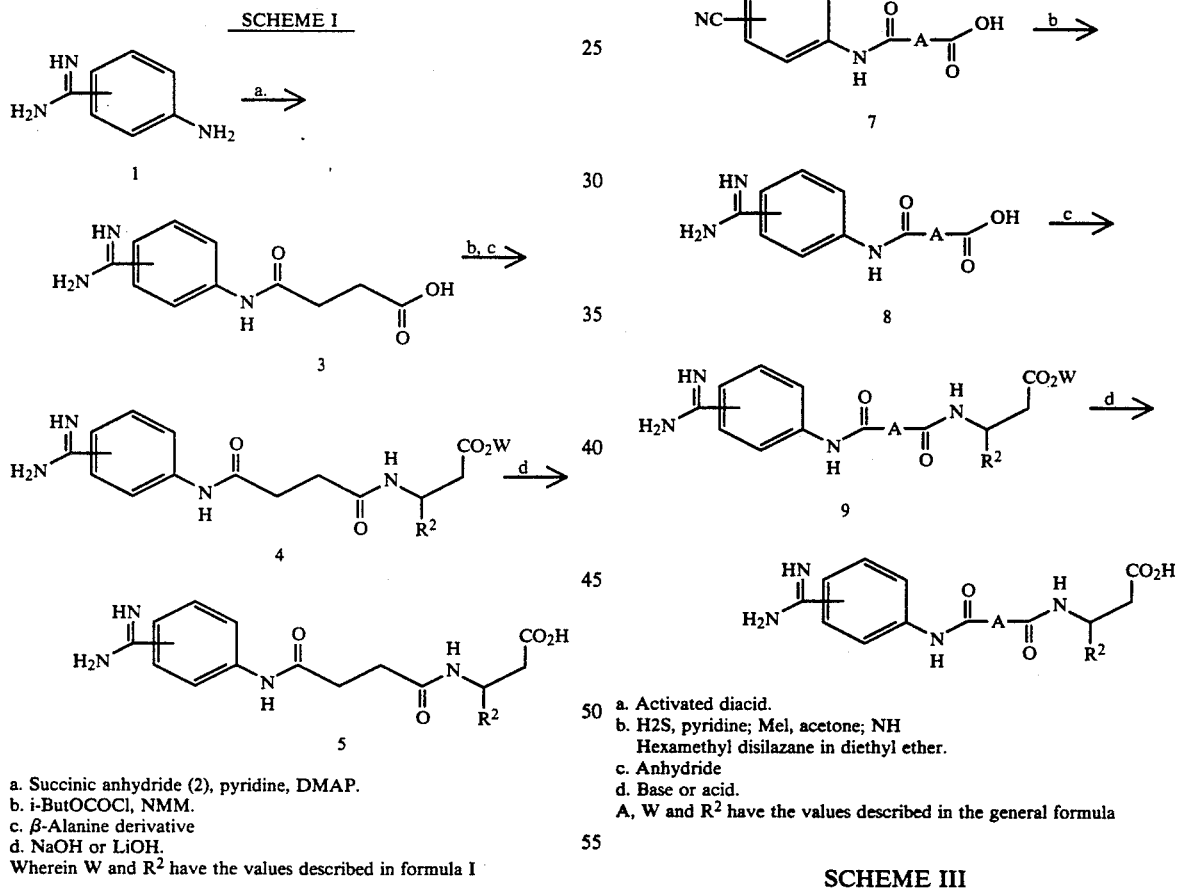

SCHEME I a. Succinic anhydride (2), pyridine, DMAP.
b. i-ButOCOCl, NMM.
c. β-Alanine derivative
d. NaOH or LiOH.
Wherein W and $R^2$ have the values described in formula I

SCHEME II a. Activated diacid.
b. $H_2S$, pyridine; MeI, acetone; NH Hexamethyl disilazane in diethyl ether.
c. Anhydride
d. Base or acid.
A, W and $R^2$ have the values described in the general formula

SCHEME II

Alternatively, an aminobenzonitrile 6, can be used for condensation with the desired diacid or diacid derivative. In that case, the nitrile can be converted to the amidine directly or at a later stage. When the aminobenzonitrile is used in the condensation reaction (Scheme II), the cyano group of the resulting intermediate 7 is converted to the amidine 8 via the thioimidate in nearly quantitative yield. The thioimidate is formed by first treating the cyano compound with hydrogen sulfide

SCHEME III

Scheme III illustrates the obtention of derivatives using the amino nitriles as reagents. The cyano group is kept unchanged as a precursor for the amidine function throughout two amide bond forming steps. The first intermediate 10 is directly engaged in a reaction with the desired amino acid. The intermediate 10 is then converted to the benzamidine. A method of choice to produce the amidine function is via the thioimidate procedure as described in Scheme II. It is desirable, in Scheme III, to prepare the intermediate 11 as an ester. The most desirable ester is the t-butyl ester which can be deprotected to the acid by contact with a strong acidic medium as HBr/AcOH or trifluoroacetic acid/dichloromethane.

SCHEME III

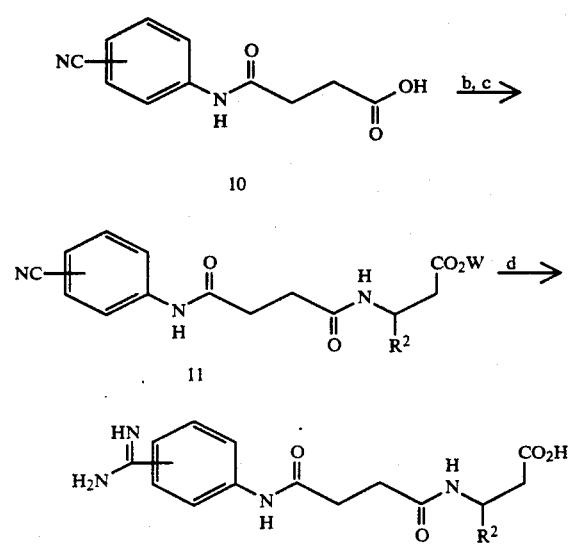

a. Succinic anhydride, pyridine, DMAP.
b. Anhydride mixte, NMM.
c. b-Allanine derivatives
d. H2S, pyridine; MeI, acetone; NH4OAc or Hexamethyl disilazane in diethyl ether.

SCHEME IV and V

Substituted aminonitrile can be used to prepare substituted N-aminobenzamidine succinyl derivatives as specifically illustrated in Scheme IV for the chloro derivative 14. The beta amino acids can be either purchased or prepared from commercially available starting materials using known methods as illustrated in Scheme V. The racemic beta aryl beta amino acids can be prepared from the appropriate arylaldehyde, malonic acid, and ammonium acetate as shown in Scheme V—method 1 (Johnson and Livak *J. Am. Chem. Soc.* 299 (1936)]. The racemic beta alkyl beta amino acids can be prepared from the corresponding alkene and chlorosulfonyl isocyanate (CSI) which goes through the beta lactam intermediate as shown in Scheme V—method 2 [W. A. Szabo *Aldrichimica Acta* 23 (1977); R. Graf *Angew, Chem. Internat. Edit.* 172 (1968)]. The beta lactam can be opened to the ethyl ester by treatment with anhydrous hydrochloric acid in ethanol as shown Scheme V. For example, 1,3-butadiene and 3-phenyl-1-propene reacted with CSI to form beta lactams and following subsequent opening with anhydrous HCl in ethanol were used in Examples 28 and 34 respectively. An alternative method to form racemic beta amino esters is shown in Scheme V method 3. Nucleophiles can be added to 4-benzoyloxy-2-azetidinone to afford a variety of 3-substitute beta amino esters after treatment with anhydrous HCl in ethanol. For example, 1-lithio-2-trimethylsilylethyne was added to 4-benzolyoxy-2-azetidinone to afford the beta amino ester of Example 36 after ring opening [for a similar reaction see D. H. Hua and A. Verma *Tetrahedron Lett.* 547–550 (1985) or T. Kametani, *Heterocycles* Vol. 17 463 (1982)]. In another example, Example 30, 4-benzolyloxy-2-azetidinone was reacted with allyltrimethylsilane under lewis acid catalysis [titanium tetrachloride-K., Prasad et al., Vol. 19 Heterocycles 2099 (1982)].

Scheme IV

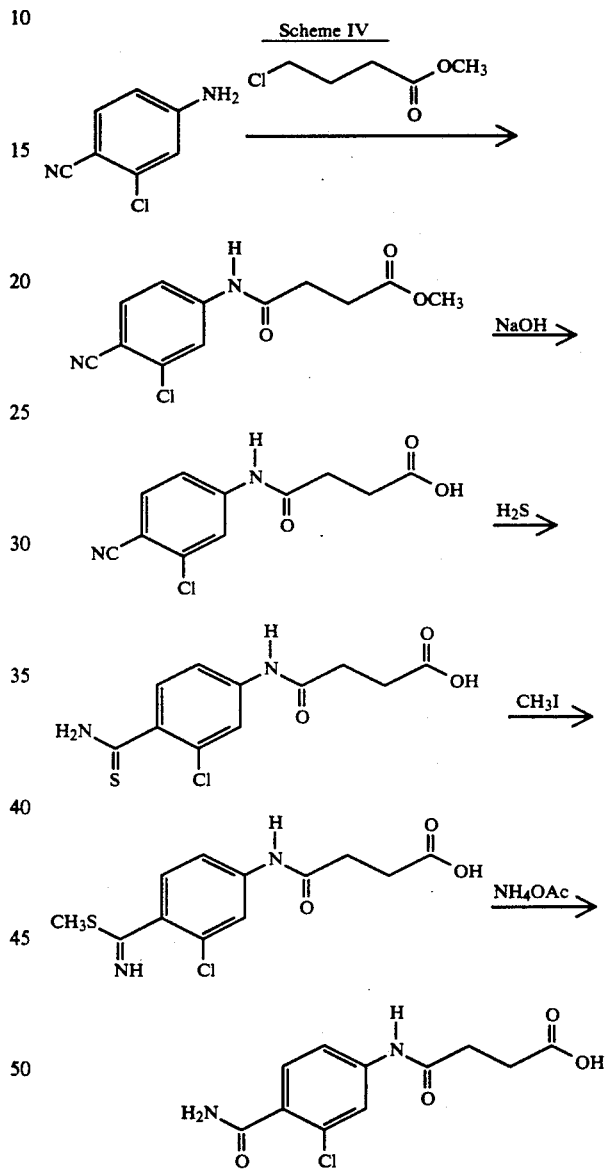

Scheme V

Method 1

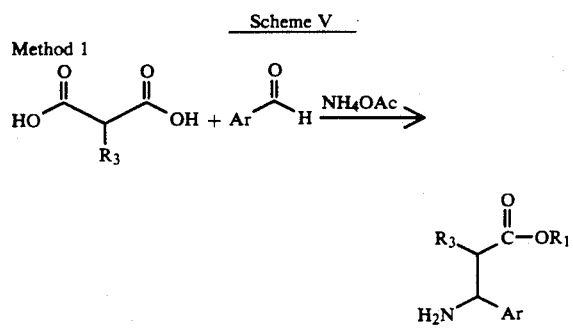

-continued
Scheme V
Method 2
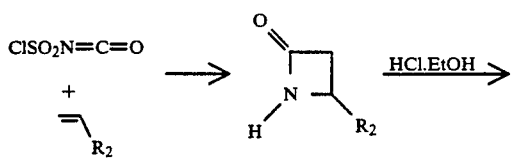
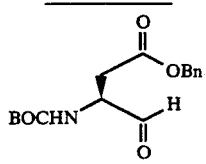
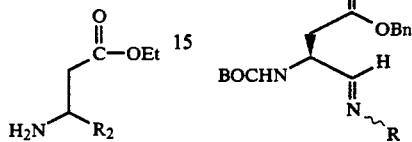
-continued
Scheme V
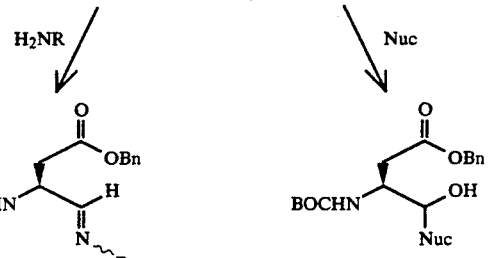
Method 3
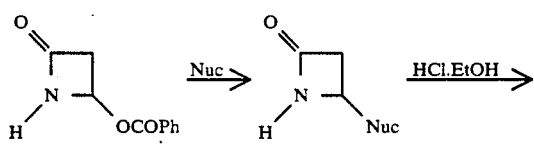
Method 6
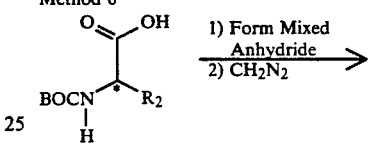
*Indicates Chiral Center
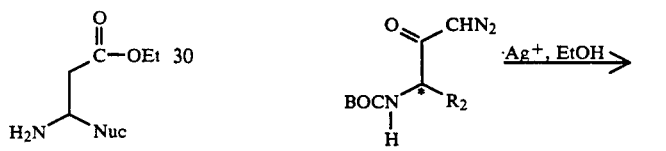
Retention of Stereochemistry
Method 4
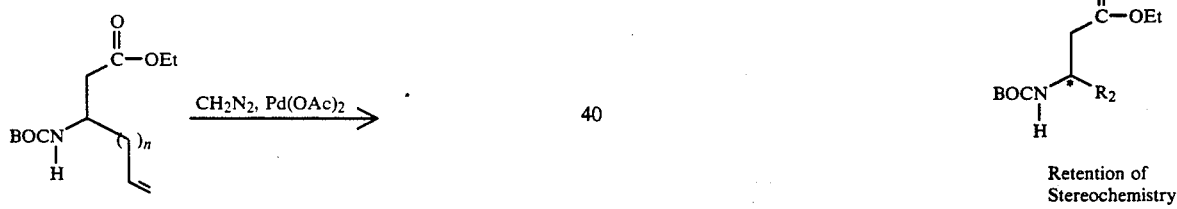
Method 7
$X_c$ = 8-(p-phenoxyphenyl)-menthyl
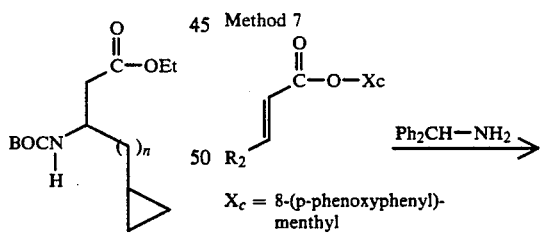
*Indicates Chiral Center
Method 5
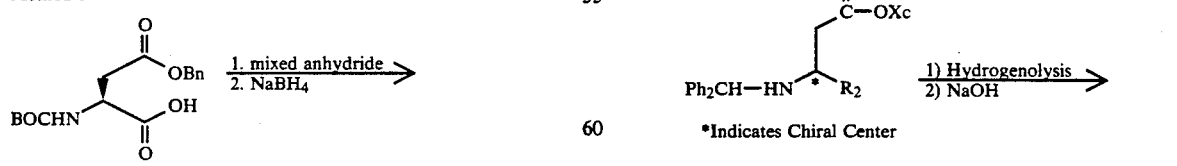
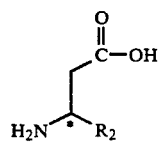
Method 8

-continued
Scheme V

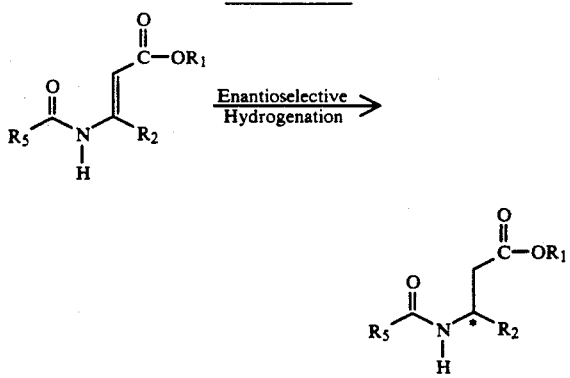

Method 9

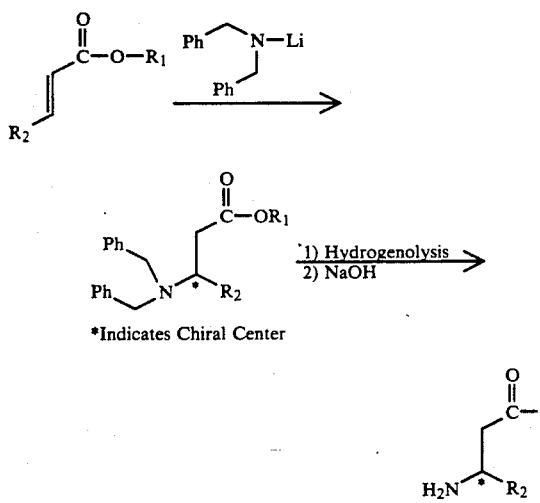

*Indicates Chiral Center

In Example 28, the cyclopropyl derivative was prepared from the corresponding vinyl compound by treatment with diazomethane and palladium acetate [U. Mande et at., *Tetrahedron Lett.* 629 (1975)] as shown in Scheme V method 4. The racemic beta amino acids can be resolved using classical methods as described in the literature [E. Fischer, H. Scheibler, R. Groh *Ber.* 2020 (1910); E. Fischer, H. Scheiber *Annalen* 337 (1911)].

Chiral beta amino acids can be prepared using many different approaches including the following methods: homologation of the alpha amino acids using an Arndt-Eistert reaction as shown in Scheme V method 5 [Meier and Zeller *Angew. Chem. Int. Ed. Eng.* 32-43 (1975)] as shown in Scheme F method 3 [M. Rodriguez et al. *Tetrahedron Lett.* 5153 (1990); W. J. Greenlee *J. Med. Chem.* 434 (1985) and references therein]; from enantiomerically pure precursors obtained from L-aspartic acid [i.e., Scheme V method 6, see: M. Rodriguez *Tetrahedron Lett.* 923 (1991)]; through the addition of chiral amines to alpha, beta unsaturated esters bearing a chiral auxiliary as shown in Scheme V method 7 [J. d'Angelo and J. Maddaluno J. Am. Chem. Soc. 8112-14 (1986)]; through an enantioselective hydrogenation of a dehydroamino acid as shown in Scheme V method 8 [see: Asymmetric Synthesis, Vol. 5, (J. D. Morrison, ed.) Academic Press, New York, 1985]; through the addition of enantiomerically pure amines to alpa, beta unsaturated esters as shown in Scheme V method 9 [see: S.

G. Davies and O. Ichihara *Tetrahedron:Asymmetry* 183-186 (1991)].

Method 6 of Scheme V was used to obtain a versatile enantiomerically pure aldehyde intermediate. The aldehyde was reacted with methoxylamine to form the oxime which was used in Example 40. The appropriate organometallic was added to the aldehyde to afford the corresponding alcohol.

The Z substituents, (where Z is hydrogen or halogen, or an alkyl radical or alkoxy radical) can be introduced at the aminobenzonitrile stage. The phenyl group can be halogenated using bromine, iodine, or chlorine. The alkyl group can be introduced by low temperature lithium halogen exchange followed by quenching with the appropriate aldehyde [see: W. E. Parham, C. K. Bradsher *Acct. Chem. Res.* 300 (1982)], the disclosure of which is hereby incorporated by reference. The resulting alcohol can be converted to alkyl by hydrogenolysis [Reductions in Organic Chemistry (M. Hudicky, ed.), John Wiley & Sons, New York, 1984], the disclosure of which is hereby incorporated by reference. Where Z is hydroxy or alkoxy, such substituents can be introduced by low temperature lithium halogen exchange followed by quenching with electrophilic bis(trimethylsilyl) peroxide [(TMSO)$_2$] M. Taddei and A. Ricci *Synthesis* 633-635 (1986)], the disclosure of which is hereby incorporated by reference, which affords the silyl ether. The silyl ether can be converted to the hydroxy derivative by treatment with hydrochloric acid [M. Taddei and A. Ricci *ibid*]. The hydroxy in the presence of a weak base (K2CO3) and an appropriate alkyl halide [R8-Hal, Allen C. F. and Gates J. W., Org. Synth. Coll. Vol 2 3 140 (1955), the disclosure of which is hereby incorporated by reference.] which will form the ester as well. The ester can be selectively cleaved in the presence of the ether with one equivalent of sodium hydroxide.

For derivatives wherein $R^1$ is different from hydrogen, such derivatives can be obtained by using an appropriately substituted aminobenzamidine. For example, the N-methylaminobenzamidine can be reacted with succinic anhydride in a manner similar to the aminobenzamidine.

Purification of final compounds is by reverse phase high pressure liquid chromatography (*High Performance Liquid Chromatography Protein and Peptide Chemistry,* F. Lottspeich, A. Henscher, K. P. Hupe, eds. Walter DeGruyter, New York, 1981, the disclosure of which is hereby incorporated by reference.) or crystallization.

Contemplated equivalents of the general formulas set forth above for the platelet aggregation inhibitors and derivatives as well as the intermediates are compounds otherwise corresponding thereto and having the same general properties wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The following preferred specific embodiments are, therefore, to be construed as merely illustrative and not limitative of the remainder of the disclosure in any way whatsoever.

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees centigrade. Within the foregoing synthetic description and examples which follow, abbreviations have the following meanings:

| | |
|---|---|
| $CHCl_3$ = | chloroform |
| DMF = | dimethylformamide |
| DMSO = | dimethylsulfoxide |
| g = | gram |
| MeOH = | methanol |
| min = | minute |
| h = | hour |
| mol = | mole |
| mmol = | mmole |
| MW = | molecular weight |
| TLC = | thin layer chromatography |
| NMM = | N-methyl morpholine |
| RPHPLC = | Reverse Phase High Pressure Liquid Chromatography |
| TDA-1 = | Tris[2(2-methoxyethoxy)ethyl]amine |
| PTC = | Phase Transfer Catalysis |

EXAMPLE 1

D,L-3-[[4-[[4-(aminoiminomethyl)phenyl]amino]-1,4-dioxobutyl]amino]3-phenylpropionic acid

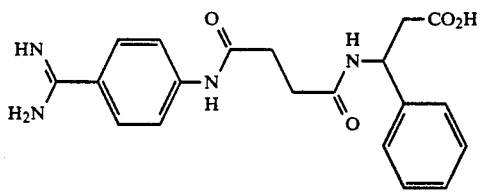

Step 1 Preparation of 4-[[4-(aminoiminomethyl)phenyl]-amino]-4-oxobutanoic acid 4-Aminobenzamidine di-HCl (25 g, 120 mmol), which is commercially available particularly from Aldrich, was added to dry DMF (100 ml). To this solution dry pyridine (100 ml) and succinic anhydride (12 g, 120 mmol) followed by dimethylaminopyridine (DMAP 1.5 g 0.012 mmol) were added. The product precipitated 20 after heating for ½h at 100° C. The product was filtered, washed with water, acetonitrile and ether. The light solid was suspended in dioxane, 4N HCl in dioxane (100 ml) was added and the suspension was stirred for 1 h, filtered and dried in a desiccator to give 28 g, 88% of 4-[[(aminoiminomethyl)phenyl]amino]-4-oxo-butanoic acid as a white yellow solid which decomposes between 270° and 290° C.

Step 2 Preparation of D,L-3-[[4-[[4-aminoiminomethyl)-phenyl]amino]-1,4-dioxobutyl]amino]3-phenylpropionic acid 4-[[4-(Aminoiminomethyl)phenyl]amino]-4-oxobutanoic acid hydrochloride prepared in Step 1 (1 g, 3.7 mmol) was added to dry DMF (35 ml) followed by N-methylmorpholine (0.39 g, 1 eq.) and isobutyl chloroformate (0.53 g, 3.9 mmol) at 25° C. The mixture was stirred for 5 min. D,L-3-Amino-3-phenylpropionic acid (0.67 g, 4.05 mmol) was added followed by diisopropylethylamine (0.68 mL; 3.9 mmol) and a catalytic amount of dimethylaminopyridine. After 1 hr the solvent was removed under reduced pressure and the product was purified by reverse phase chromatography (water/acetonitrile) and lyophilized to give 340 mg of white solid: 1H NMR (d$_6$-DMSO) δ 2.45 (m, 2H), 2.6 (m, 2H), 2.7 (d, 2H, J=7 Hz), 4.2 (dd, 1H, J=7 Hz and 8 Hz), 7.3 (m, 4H), 7.8 (s, 4H), 8.45 (d, 1H, J=8 Hz), 9.0 (bs, 2H), 9.2 (bs, 2H), 10.4 (s, 1H); MS (FAB) m/e 383.2(M+H+).

Elemental Analysis Required for $C_{20}H_{22}N_4O_4 \cdot F_3O_2H \cdot H_2O$: C 51.36, H 4.90. N 10.90. Found: C 51.67, H 4.74, N 10.72.

EXAMPLE 2

D,L-3-[[4-[[4-aminoiminomethyl)phenyl]amino]-1,5-dioxopentyl]amino]-3-phenylpropionic acid

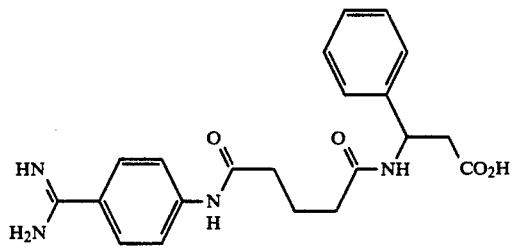

Step 1 Preparation of 4-[[4-(aminoiminomethyl)phenyl]-amino]-5-oxopentanoic acid 4-Aminobenzamidine di-HCl (1 g, 4.8 mmol) was added to dry DMF (20 mL). To this solution dry pyridine (5 mL) and glutaric anhydride (0.68 g, 5.3 mmol) followed by 10 mg dimethylaminopyridine (DMAP) were added. The product started to precipitate after heating for ½h at 100° C. Heating was continued for 2 hr and water (25 mL) was added after cooling to room temperature. An abundant precipitate was filtered and dried in a desiccator to give 0.8 g, 50% of product as a white solid: H NMR (d$_6$-DMSO) δ 1.95 (m, 2H), 2.4 (m, 2H), 2.5 (m, 2H), 7.85 (s, 4H), 9.05 (bs, 2H), 9.25 (bs, 2H), 10.4 (s, 1H), MS(FAB) m/e 250.1 (M+H+).

Step 2 Preparation of D,L-3-[[4-[[4-(aminoiminomethyl)-phenyl]amino]1,5-dioxopentyl]amino]-3-phenylpropionic acid An aliquot of 4-[[4-(aminoiminomethyl)phenyl-]amino]-5-oxopentanoic acid prepared in Step 1 (1 g, 3.5 mmol) was dissolved in dry DMF (35 ml) and N-methylmorpholine (0.39 g, 1 eq.) and isobutyl chloroformate (0.5 g) were added to the mixture cooled to 0°

C. The mixture was stirred for 5 min. D,L-3-Amino-3-phenylpropionic acid (0.58 g) was added followed by a catalytic amount of dimethylaminopyridine. After 1 h the solvent was removed under reduced pressure and the product was purified by reverse phase chromatography (water/acetonitrile) to give 440 mg of white fluffy solid: $^1$H NMR (d$_6$-DMSO) δ 1.80 (m, 2H), 2.18 (t, 2H, J=7 Hz), 2.4 (t, 2H, J=7 Hz), 2.65 (d, 2H, J=7 Hz), 4.2 (dd, 1H, J=7 Hz and 8 Hz), 7.3 (m, 4H), 7.8 (s, 4H), 8.35 (d, 1H, J=8 Hz), 8.95 (bs, 2H), 9.18 (bs, 2H), 10.34 (s, 1H); MS (FAB) m/e 397.2(M+H+), 351, 232.

Elemental Analysis Required for C$_{21}$H$_{24}$N$_4$O$_4$.F$_3$C$_2$O$_2$H.H$_2$O: C 52.27, H 5.15, N 10.60. Found: C 52.19, H 5.12, N 10.38.

EXAMPLE 3

D,L-3-[[4-[[4-(aminoiminomethyl)phenyl]amino]-1,4-dioxobutyl]amino]-butanoic acid

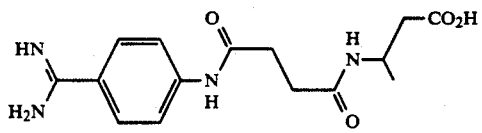

An aliquot of 4-[[4-(aminoiminomethyl)phenyl]amino]-4-oxobutanoic acid prepared in Example 1, Step 1 (2 g) was added to dry DMF (65 ml) followed by N-methylmorpholine (0.75 g, 1 eq.) and isobutyl chloroformate (1 g) at 25° C. The mixture was stirred for 5 min. 3-Aminobutyric acid (1.1 g, 1.1 eq.) was added followed by triethylamine (1.5 g, 1.3 eq.) and dimethylaminopyridine. After 1 h the solvent was removed under reduced pressure and the product was purified by reverse phase chromatography (water/acetonitrile) to give 750 mg of white solid: $^1$H NMR (d$_6$-DMSO) δ 1.06 (d, 3H, J=7 Hz), 2.2-2.6 (m, 6H), 4.05 (m, 1H), 7.8 (m, 4H), 7.85 (d, 1H, J=8 Hz), 9.05 (bs, 2H), 9.15 (bs, 2H), 10.4 (s, 1H); MS (FAB) m/e 321.1(M+H+), 236.

Elemental Analysis Required for C$_{15}$H$_{20}$N$_4$O$_4$.F$_3$C$_2$O$_2$H.0.75H$_2$O: C 45.66, H 4.90, N 12.52. Found: C 45.54, H 4.27, N 12.41.

EXAMPLE 4

D,L-ethyl-3-[[4-[[4-(aminoiminomethyl)phenyl]amino]-1,4-dioxobutyl]amino]-butanoate

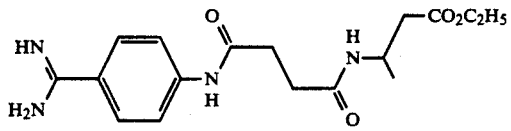

4-[[4-(aminoiminomethyl)phenyl]amino]-4-oxobutanoic acid hydrochloride prepared in Example 1, Step 1 (5 g, 18 mmol) was added to dry DMF (100 ml) followed by N-methylmorpholine (2.2 g, 22 mmol) and isobutyl chloroformate (2.8 g, 22 mmol) at 25° C. The mixture was stirred for 5 min. Ethyl 3-amino butyrate (2.5 g, 22 mmol) was added followed by dimethylaminopyridine. After 1 hr the solvent was removed under reduced pressure and the product was purified by reverse phase chromatography (water/acetonitrile) to give 4.4 g of white solid: $^1$H NMR (d$_6$-DMSO) δ 1.06 (d, 3H, J=7 Hz), 2.3-2.6 (m, 6H), 4.05 (m, 3H), 7.8 (s, 4H), 7.9 (d, 1H, J=8 Hz), 9.1 (bs, 2H), 9.2 (bs, 2H), 10.4 (s, 1H); MS (FAB) m/e 349.2 (M+H+), 321, 218.

Elemental Analysis Required for C$_{17}$H$_{24}$N$_4$O$_4$.F$_3$C$_2$O$_2$H: C 49.35, H 5.44, N 12.11. Found: C 49.18, H 5.44, N 11.98.

EXAMPLE 5

Ethyl-3-[[4-[[4-(aminoiminomethyl)phenyl]amino]-1,4-dioxobutyl]amino]propanoate

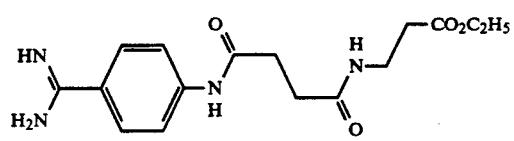

An aliquot of 4-[[4(aminoiminomethyl)phenyl]amino]-4-oxobutanoic acid hydrochloride prepared in Example 1, Step 1 (1.36 g) was added to dry DMF (50 ml) followed by N-methylmorpholine (0.6 mL) and isobutyl chloroformate (0.65 mL) at 0° C. under nitrogen atmosphere. The mixture was stirred for 5 min 0.45 g β-alanine ethyl ester hydrochloride was added followed by 0.6 mL of N-methyl morpholine. After 4 hr the solvent was removed under reduced pressure and the product was purified by reverse phase chromatography (water/acetonitrile) to give 4.4 g of white solid: $^1$H NMR (d$_6$-DMSO) δ 1.2 (t, 3H, J=7 Hz), 2.45 (m, 4H), 2.6 (m, 2H), 3.25 (m, 2H), 4.05 (q, 2H, J=7 Hz), 7.8 (s, 4H), 8.0 (m, 1H), 8.85 (bs, 2H), 9.18 (bs, 2H), 10.4 (s, 1H); MS (ES) m/e 335.1(M+H+).

Elemental Analysis Required for C$_{16}$H$_{22}$N$_4$O$_4$.1.5F$_3$C$_2$O$_2$H.05H$_2$O: C 43.21, H 4.53, N 11.20. Found: C 43.56, H 4.70, N 11.07.

EXAMPLE 6

3-[[4-[[4-(aminoiminomethyl)phenyl]amino]-1,4-dioxobutyl]amino]propionic acid)

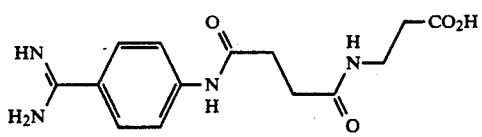

A portion of ethyl-3-[[4-[[4-aminoiminomethyl)phenyl]amino]-1,4dioxobutyl]amino]propanoate (300 mg) was dissolved in 10 mL water. Sodium hydroxide (2N) was added until the pH reached 10. The reaction mixture was allowed to stir at 25° C. for 30 min during which time a precipitate appeared. The mixture was acidified with HCl to pH 5. The precipitate was filtered, washed with water and diethyl ether and purified by RPHPLC (acetonitrile/water) to give 50 mg of a white powder: $^1$H NMR (d$_6$-DMSO) δ 2.4 (m, 4H), 2.6 (m, 2H), 3.25 (m, 2H), 7.8 (s, 4H), 8.0 (t, 1H, J=7 Hz), 8.80 (bs, 2H), 9.18 (bs, 2H), 10.4 (s, 1H); MS (ES) m/e 307.1(M+H+).

Elemental Analysis Required for C$_{14}$H$_{18}$N$_4$O$_4$.F$_3$C$_2$O$_2$H.0.5H$_2$O: C 44.86, H 4.47, N 13.08. Found: C 45.03, H 4.55, N 12.99.

EXAMPLE 7

Preparation of
D,L-ethyl-3-[[4-[[4-(aminomethyl)-phenyl]amino]-1,4-dioxobutyl]amino]-3-phenylpropanoate

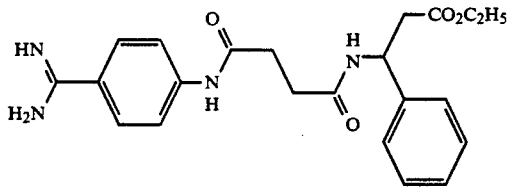

In a round bottom flask under a static atmosphere of dry nitrogen were mixed 1.3 g of D,L-3-[[4-[[4-(aminoiminomethyl)phenyl]amino]-1,4-dioxobutyl]amino]-3-phenylpropanoic acid prepared as described in Example 1, Step 2, 200 mL absolute ethanol and 10 mL 4 N HCl in dioxane. The reaction mixture was stirred at 25° C. for 16 hr. The volatiles were removed in vacuo and the remaining white solid was purified by RPHPLC (water/acetonitrile gradient; 95/5 to 30/70 over 30 min) to provide 0.62 g of the desired ester as a white solid: $^1$H NMR (d$_6$-DMSO) $\delta$ 1.1 (t, 3 H, J=7 Hz), 2.45 (m, 2H), 2.6 (m, 2H), 2.75 (d, 2H, J=7 Hz), 4.0 (q, 2H, J=7 Hz), 4.2 (dd, 1H, J=7 Hz and 8 Hz), 7.3 (m, 4H), 7.8 (s, 4H), 8.45 (d, 1H, J=8 Hz), 9.05 (bs, 2H), 9.2 (bs, 2H), 10.4 (s, 1H); MS (FAB) m/e 411.2(M+H+), 135.2.

Elemental Analysis Required for C$_{22}$H$_{26}$N$_4$O$_4$.F$_3$O$_2$H.H$_2$O: C 53.13 H 5.41 N 10.24. Found: C 53.13, H 5.39, N 10.33.

EXAMPLE 8

3-[[4-[[4-(aminoiminomethyl)phenylamino]-1,4-dioxobuten-(Z)-yl]amino]-phenylpropanoic acid

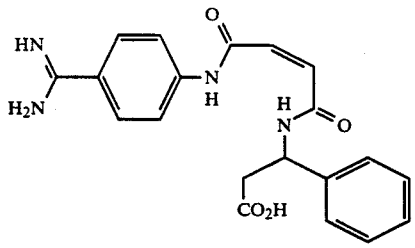

The compound was prepared from maleic anhydride, aminobenzamidine and 3-amino phenylpropionic acid in a manner similar to that described in Example 1. $^1$H NMR (d$_6$-DMSO) $\delta$ 2.45 (m, 2H), 3.6 (m, 2H), 7.05 (m, 2H), 7.85 (m, 4H), 8.6 (m, 1H), 8.9 (bs, 2H), 9.1 (d, 1H, J=7 Hz), 9.25 (bs, 2H), 10.85 (s, 1H); MS (ES) m/e 381.2(M+H+), 216.

Elemental Analysis Required for C$_{20}$H$_{20}$N$_4$O$_4$.F$_3$-C$_2$O$_2$H.1.5H$_2$O: C, 50.67, H 4.64, N 10.74. Found: C 50.28, H 4.15, N 10.63.

EXAMPLE 9

3-[[4-[[4-(aminoiminomethyl)phenyl]amino]-1,4-dioxobuten-(E)-yl]amino]-propanoic acid

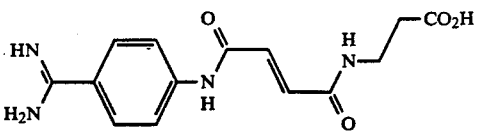

Step 1 Preparation of
4-[[4-(aminoiminomethyl)phenyl]amino]-4-oxo-buten-(E)-oic acid In a round bottomed flask under a static atmosphere of dry nitrogen were mixed 1.4 g of monoethyl fumarate, 1.36 g of isobutyl chloroformate and 1.01 g N-methylmorpholine in 100 mL DMF. 4-aminobenzamidine dihydrochloride (2.06 g) and 2.02 g N-methylmorpholine were added at room temperature and the reaction mixture was stirred at 25° C. for 30 min. Water and sodium hydroxide were added to pH 10 and after one hour stirring neutralized to pH 7 to precipitate the zwitterion. Filtration provided 1 g of the desired compound as a white solid: $^1$H NMR (d$_6$-DMSO) $\delta$ 1.1 (t, 3 H, J=7 Hz), 2.45 (m, 2H), 2.6 (m, 2H), 2.75 (d, 2H, J=7 Hz), 4.0 (q, 2H, J=7 Hz), 4.2 (dd, 1H, J=7 Hz and 8 Hz), 7.3 (m, 4H), 7.8 (s, 4H), 8.45 (d, 1H, J=8 Hz), 9.05 (bs, 2H), 9.2 (bs, 2H), 10.4 (s, 1H).

Step 2 Preparation of
ethyl-3-[[4-[[4-(aminoiminomethyl)phenyl]amino]-1,4-dioxobuten-(E)-yl]amino]-propanoate 4-[[4-(aminoiminomethyl)phenyl]amino]-4-oxobuten-(E)-oic acid prepared in Example 9, Step 1 (1.35 g) was added to dry DMF (50 ml) followed by N-methylmorpholine (0.55 mL) and isobutyl chloroformate (0.65 mL) under nitrogen atmosphere. The mixture was stirred for 5 min and 0.75 g of B-alanine ethyl ester hydrochloride were added followed by 0.55 mL of N-methylmorpholine. After 2 hr the solvents were removed under reduced pressure and the product was purified by reverse phase chromatography (water/acetonitrile) to give 700 mg of white solid.

Step 3
3-[[4-[[4-(Aminoiminomethyl)phenyl]amino]-1,4-dioxobuten-(E)-yl]amino]-propanoic acid A portion of ethyl 3-[[4-[[4-(aminoiminomethyl)-phenyl]amino]-1,4-dioxobuten-(Z)-yl]amino]-propanoate (150 mg of the trifluoroacetate salt) prepared as in Example 9, step 2 was dissolved in 10 mL water and 10 mL acetonitrile and 5 drops of 50% sodium hydroxide were added. The reaction mixture was allowed to stir at 25° C. for 1 hr and was acidified to pH 5. The precipitate was collected by filtration, washed with acetonitrile, water, and diethylether to give 120 mg of a white powder which was lyophilized from HCl to give the hydrochloride salt: $^1$H NMR (d$_6$-DMSO) d 2.45 (m, 2H), 3.6 (m, 2H), 7.0 (m, 2H), 7.85 (m, 4H), 8.63 (m, 1H), 8.85 (bs, 2H), 9.20 (bs, 2H), 10.9 (s, 1H); MS (ES) m/e 333.1(M+H+).

Elemental Analysis Required for C$_{14}$H$_{17}$N$_4$O$_4$.1.5 F$_3$C$_2$O$_2$H.0.5H$_2$O: C 41.39, H 3.98, N 11.36. Found: C 41.55, H 3.83, N 11.72.

EXAMPLE 10

Preparation of
D,L-3-[[4-[[4-(aminoiminomethyl)phenyl]amino]-1,4-dioxobutyl]amino]-3-(2-hydroxyphenyl)propanoic acid

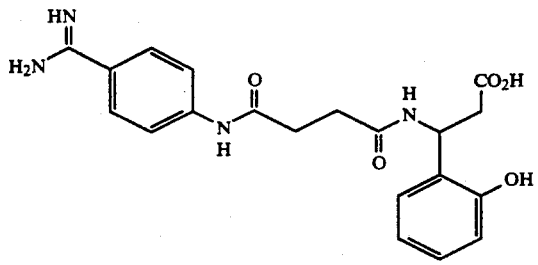

In a flask under nitrogen, the succinyl derivative prepared in Example 1, Step 1 (5.7 g) was activated with isobutyl chloroformate (2.9 g) and coupled with 4.2 g of 3-amino-3,4-dihydro-2-oxo-2H-1-benzopyrane hydrochloride in a manner similar to Step 2, Example 1. The reaction mixture was worked up as usual and the product purified by reverse phase HPLC to give 2.9 g of 3-[[4-[[4-(aminoiminomethyl)phenyl]amino]-1,4-dioxobutyl]amino]-3-(2-hydroxyphenyl) propanoic acid as a white powder: $^1$H NMR (d$_6$-DMSO) d 2.5 (m, 6H), 4 (m, 1H), 6.7 (t, 1H, J=7.5 Hz), 6.8 (d, 1H, J=7.5 Hz), 7.05 (t, 1H, J=7.5 Hz), 7.2 (d, 1H, J=7.5 Hz), 7. 8 (s, 4H), 8.25 (d, 1H, J=8 Hz), 8.95 (bs, 2H), 9.2 (bs, 2H), 10.4 (s, 1H); MS (FAB) m/e 399.1 (M+H+), 235.

Elemental Analysis Required for $C_{20}H_{22}N_4O_5.F_3.C_2O_2H.2H_2O$: C 48.25, H 4.95, N 10.25. Found: C 48.72, H 5.56, N 10.21.

EXAMPLE 11

D,L-3-[[4-[[4-(aminoiminomethyl)phenyl]amino]2-(3)-methyl-1,4-dioxobutyl]amino]-3-phenylpropionic acid

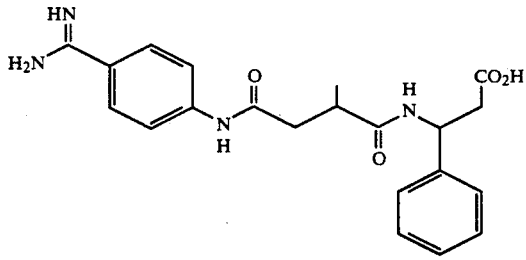

Step 1 preparation of 4-[[4-(aminoiminomethyl)phenyl]amino]-2(3)-methyl-4-oxobutanoic acid A procedure similar to Step 1 of Example 1 using 5 g of aminobenzamidine di-HCL and 2.85 g methyl succinic anhydride was used. The product was filtered, washed with water, acetonitrile and ether. The white solid (4.5 g) was suspended in dioxane, 4N HCl in dioxane (100 ml) was added and the suspension was stirred for 1 h, filtered and dried.

Step 2 Preparation of D,L-3-[[4-[[4-(aminoiminomethyl)phenyl]amino]-2(3)-methyl-1,4-dioxobutyl]amino]-3-phenylpropionic acid N-2(3)Methylsuccinimidyl-aminobenzamidine hydrochloride prepared in Step 1 (1.68 g, 5.8 mmol) was activated with isobutyl chloroformate (0.78 mL, 6 mmol) and coupled with D,L-3-amino-3-phenylpropionic acid (0.96 g, 5.8 mmol) in a manner similar to Example 12. After usual work up, the reaction mixture was purified by reverse phase chromatography (water-/acetonitrile). Two peaks (A and B) were isolated and lyophilized. Peak A gave 340 mg of yellow solid : $^1$H NMR (d$_6$-DMSO) δ 1.0 (m, 3H); 2.4-2.6 (m, 4H), 2.8 (m, 2H), 4.1 (m, 1H), 7.15 (m, 4H), 7.7 (s, 4H), 8.45 (m, 1H), 9.0 (bs, 2H), 9.2 (bs, 2H), 10.4 (d, 1H, 8 Hz); MS (FAB) m/e 397.3(M+H+).

Elemental Analysis Required for $C_{23}H_{27}N_4O_7.F_3.C_2O_2H.1.5H_2O$: C 51.40, H 5.25, N 10.42. Found: C 51.69, H 4.86, N 10.38.

EXAMPLE 12

D,L-3-[[4-[[4-(aminoiminomethyl)phenyl]amino]-3(2)-methyl-1,4-dioxobutyl]amino]-3-phenylpropionic acid

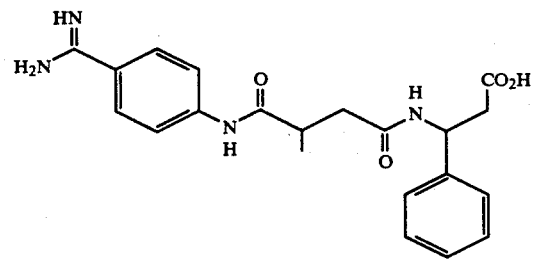

N-2(3)Methylsuccinimidyl-aminobenzamidine hydrochloride prepared in Step 1 (1.68 g, 5.8 mmol) was activated with isobutyl chloroformate (0.78 mL, 6 mmol) and coupled with D,L-3-amino-3-phenylpropionic acid (0.96 g, 5.8 mmol) in a manner similar to Step 2 of Example 1. After usual work up, the reaction mixture was purified by reverse phase chromatography (water/acetonitrile). Two peaks (A and B) were isolated and lyophilized. Peak A was described in Example 13 Step 2. Peak B isolated from the crude reaction mixture of Example 13, Step 2 gave 540 mg of white solid: $^1$H NMR (d$_6$-DMSO) δ 1.05 (m, 3H) 2.2-2.6 (m, 5H), 2.85 (m, 1H), 5.15 (m, 1H), 7.2 (m, 1H), 7.25 (s, 4H), 7.8 (s, 4H), 8.45 (m, 1H), 8.75 (bs, 2H), 9.15 (bs, 2H), 10.4 (bs, 1H); MS (FAB) m/e 397.3(M+H+).

EXAMPLE 13

Dimethyl 3-[[4-[[4-(aminoimino-methyl)phenyl]amino]-1,4-dioxobutyl]amino]pentanedioate

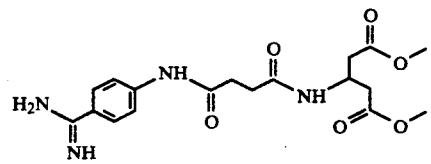

Step 1 Preparation of dimethyl-3-aminoglutarate

Dimethyl-3-oxoglutarate (10 g, 57 mmol) was added to methanol (225 ml) followed by ammonium formate (36 g, 570 mmol) and NaBH$_3$CN (3.7 g, 57 mmol) at 25° C. After 24 h the methanol was removed in vacuo to leave a white mass. Methylene chloride was added and the mixture filtered. The methylene chloride was evaporated resulting in an oil 1N HCl which was dissolved in 1N HCl (200 ml) and extracted with ether (100 ml).

The ether layer was discarded and the aqueous layer was made basic using solid $K_2CO_3$. The product was extracted into methylene chloride dried over $Na_2SO_4$ and evaporated to give dimethyl-3-aminoglutarate (7.5 g). $^1$H NMR (d6-DMSO) δ 1.76 (bs, 2H), 2.45 (dd, 4H, J=8.08 Hz, 16.64 Hz), 3.69 (s, 6H), 5.45 (m, 1H); MS (FAB) m/e 176.0 (M+H+).

Step 2 Preparation of dimethyl 3-[[4-[[4-(aminoiminomethyl)phenyl]-amino]-1,4-dioxobutyl]amino]pentanedioate 4-[[4-(aminoiminomethyl)phenyl]-amino]-4-oxobutanoic acid hydrochloride prepared in Example 1, Step 1 (4.6 g, 17 mmol) was added to dry DMF (225 ml) followed by N-methylmorpholine (1.2 g, 17 mmol) and isobutyl chloroformate (2.3 g, 17 mmol) at 25° C. The mixture was stirred for 5 min. Dimethyl-3-aminoglutarate (3.0 g, 17 mmol) was added followed by dimethylaminopyridine. After 1 hr the solvent was removed under reduced pressure and the product purified by reverse phase chromatography (water/acetonitrile) to result in 3.5 g of a white solid: $^1$H NMR (d6-DMSO) δ 2.37 (t, 2H, J=7.3 Hz), 2.55 (m, 2H), 2.57 (t, 2H, J=7.1 Hz), 3.57 (s, 6H), 4.35 (m, 1H), 7.79 (s, 4H), 7.99 (d, Hz), 9.1 (bs, 2H), 9.19 (bs, 2H), 10.42 (s, 1H); MS (FAB) m/e 393.2 (M+H+).

Elemental Analysis Required for $C_{18}H_{24}N_4O_6 \cdot F_3C_2O_2H \cdot H_2O$: C 47.42, H 4.91, N 11.14. Found: C 47.12, H 4.97, N 10.99.

EXAMPLE 14

3-[[4-[[4-(aminoiminomethyl)phenyl]-amino]-1,4-dioxobutyl]amino]pentanedioic acid, monomethylester

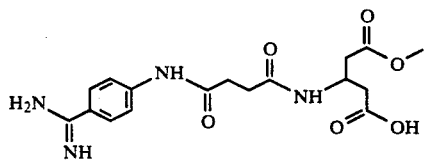

Dimethyl 3-[[4-[[4-(aminoiminomethyl)phenyl]amino]-1,4-dioxobutyl]amino]pentanedioate prepared in Example 13, Step 2 (700 mg) was added to water/acetonitrile (20 ml) followed by lithium hydroxide (100 mg) at 25° C. The mixture was stirred for 30 min. The course of the reaction was monitored by RPHPLC. After satisfactory monoester was formed the reaction was neutralized with TFA and purified by reverse phase chromatography (water/acetonitrile) to result in 460 mg white solid: $^1$H NMR (d6-DMSO) δ 2.39 (t, 2H, J=7.3 Hz), 2.55 (m, 2H), 2.57 (t, 2H, J=7.1 Hz), 3.57 (s, 3H), 4.32 (m, 1H), 7.78 (s, 4H), 7.99 (d, 1H, J=8.1 Hz), 8.92 (bs, 2H), 9.16 (bs, 2H), 10.39 (s, 1H); MS (FAB) m/e 379.2 (M+H+).

Elemental Analysis Required for $C_{17}H_{22}N_4O_6 \cdot F_3C_2O_2H \cdot H_2O$: C 45.92, H 4.63, N 11.28. Found: C 45.88, H 4.34, N 10.69.

EXAMPLE 15

3-[[4-[[4-(aminoiminomethyl)phenyl]amino]-1,4-dioxobutyl]amino]pentanedioic acid

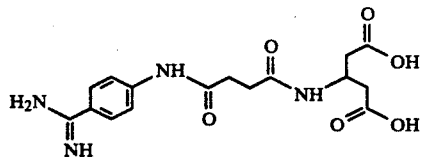

Dimethyl 3-[[4-[[4-(aminoiminomethyl)phenyl]amino]-1,4-dioxobutyl]amino]pentanedioate prepared in Example 13, Step 2 (700 mg) was added to water/acetonitrile (20 ml) followed by lithium hydroxide 100 mg) at 25° C. The mixture was stirred for 30 min. The course of the reaction was monitored by RPHPLC. After satisfactory monoester was formed the reaction was neutralized with TFA and purified by reverse phase chromatography (water/acetonitrile) to result in 620 mg of a white solid: 1H NMR (d6-DMSO) δ 2.38 (t, 2H, J=7.3 Hz), 2.44 (d, 2H, J=6.4 Hz), 2.56 (t, 2H, J=7.3 Hz), 4.32 (m, 1H), 7.78 (s, 4H), 7.99 (d, 1H, J=8.1 Hz), 8.92 (bs, 2H), 9.16 (bs, 2H), 10.39 (s, 1H); MS (FAB) m/e 365.2 (M+H+).

Elemental Analysis Required for $C_{16}H_{20}N_4O_6 \cdot F_3C_2O_2H \cdot H_2O$: C 43.54, H 4.64, N 11.13. Found: C 43.40, H 4.52, N 11.18.

EXAMPLE 16

3R-[[4-[[4-(aminoiminomethyl)phenyl]-amino]-1,4-dioxobutyl]amino]-4-cyanobutanoic acid

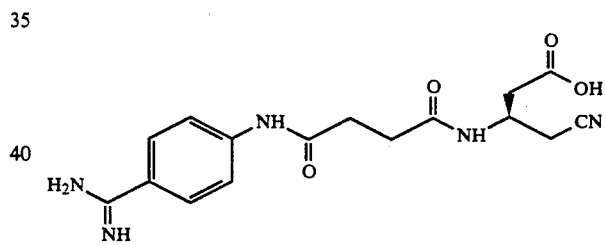

Step 1 Preparation of benzyl-3-amino-4-cyano butyrate

Benzyl-3-N-t-Boc-amino-4-hydroxy-(3S)-butyrate (20 g, 64.7 mmol) was dissolved in 200 ml of methylene chloride followed by triethylamine (9.8 g, 97 mmol) and cooled to 0° C. Methane sulfonyl chloride (9.6 g, 84 mmol) was added and the solution was stirred for 2-3 hr. After this time more methylene chloride (100 ml) was added and the solution was washed with water, and dried over $MgSO_4$ to give 27 g of the mesylate after removal of the solvent. 1H NMR (d6-DMSO) δ 1.45 (s, 9H), 2.71 (d, 2H,J=6 Hz), 2.95 (s, 3H), 4.37 (bs, H), 4.7 (bs, 2H), 5.15 (s, 2H), 7.37 (bs, 5H).

The mesylate (27 g, 64 mmol) isolated above was added to dry DMF followed by KCN, 18-crown-6, catalytic DMAP and heated at 70° C. for 2-3 h. After complete reaction, water was added and the product was extracted with ether (2×150 ml). The ether extracts were washed with water, then dried over $MgSO_4$, and the solvent evaporated to give benzyl-3-N-tBoc-amino-4-cyano-(3S)-butyrate (22 g).

The crude benzyl-3-N-tBoc-amino-4-cyano-(3S)-butyrate was dissolved in dioxane (100 ml) then to this solution 4N HCl in dioxane was added. After 6 h the dioxane was removed in vacuo to leave an oil which was dissolved in water (200 ml) and extracted with the (100 ml). The ether layer was discarded and the aqueous layer was made basic using solid $K_2CO_3$. The product was extracted into methylene chloride dried over $Na_2SO_4$ and evaporated to give benzyl-3-amino-4-cyano-(3S)-butyrate (8 g). 1H NMR (d6-DMSO) δ 1.6 (bs, 2H), 2.5-2.7 (m, 4H), 3.5 (m, 1H), 5.16 (s, 2H), 7.36 (bs, 5H); H), 4.05 (m, 3H), 7.8 (s, 4H); MS (FAB) m/e 219.0 (M+H+).

Step 2 Preparation of 3R-[[4-[[4-(aminoiminomethyl)phenyl]-amino]-1,4-dioxobutyl]aminobutyl]amino]-4-cyanobutanoic acid 4-[[4-(aminoiminomethyl)phenyl]-amino]-4-oxobutanoic acid hydrochloride prepared in Example 1, Step 1 (5.1 g, 18.9 mmol) was added to dry DMF (250 ml) followed by N-methylmorpholine (1.8 g, 18.9 mmol) and isobutyl chloroformate (2.7 g, 18.9 mmol) at 25° C. The mixture was stirred for 5 min. Benzyl-3-amino-4-cyano butyrate (3.0 g, 18.9 mmol; from Step 1) was added followed by dimethylaminopyridine. After 1 h the solvent was removed under reduced pressure and the product purified by reverse phase chromatography (water/acetonitrile) to result in 3.5 g of a white solid. A portion of this material was then subjected to saponification conditions as previously described and purified by reverse phase chromatography (water/acetonitrile) to result in 425 mg of a white solid: 1H NMR (d6-DMSO) δ 2.44 (m, 2H), 2.5 (m, 2H), 2.60 (m, 2H), 2.74 (dd, 2H, J=6.9, 11.8 Hz), 4.25 (m, 1H), 7.78 (s, 4H), 8.26 (d, 1H, J=7.7 Hz), 8.89 (bs, 2H), 9.14 (bs, 2H), 10.40 (s, 1H); MS (FAB) m/e 346.1 (M+H+).

Elemental Analysis Required for $C_{16}H_{19}N_5O_4.F_3.C_2O_2H.H_2O$: C 46.15, H 4.48, N 14.95. Found: C 46.15, H 4.28, N 14.76.

EXAMPLE 17

(±)-Diethyl-3-[[4-[[4-(aminoiminomethyl)phenyl]-amino]-4-dioxobutyl]amino]heptanedioate

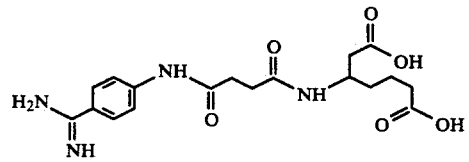

Step 1 Preparation of diethyl-3-aminopimaleate

Diethyl-3-oxopimaleate (10 g, 43 mmol) was added to methanol (225 ml) followed by ammonium formate (27.4 g, 430 mmol) and $NaBH_3CN$ (2.7 g, 43 mmol) at 25° C. After 24 h the methanol was removed in vacuo to leave a white mass. Methylene chloride was added and the mixture filtered. The methylene chloride was evaporated resulting in an oil which was dissolved in 1N HCl (200 ml) and extracted with ether (100 ml). The ether layer was discarded and the aqueous layer was made basic using solid $K_2CO_3$. The product was extracted into methylene chloride dried over $Na_2SO_4$ and evaporated to give diethyl-3-aminopimaleate (7.5 g). 1H NMR (d6-DMSO) δ 1.25 (t, 3H, J=7 Hz), 1.26 (t, 3H, J=8 Hz), 1.45 (m, 2H), 1.7 (m,2H), 2.01 (bs, 2H), 2.45 (m, 2H), 3.2 (m, 1H), 4.13 (q, 4H, J=8 Hz); MS (FAB) m/e 132.1 (M+H+) 186.2.

Step 2 Preparation of (±)-diethyl-3-[[4-[[4-(aminoiminomethyl)phenyl]-amino]-1,4-dioxobutyl]amino]heptanedioate 4-[[4-(Aminoiminomethyl)phenyl]-amino]-4-oxobutanoic acid hydrochloride prepared in Example 1, Step 1 (5.0 g, 18.5 mmol) was added to dry DMF (250 ml) followed by N-methylmorpholine (2.2 g, 18.5 mmol) and isobutyl chloroformate (2.7 g, 18.5 mmol) at 25° C. The mixture was stirred for 5 min. Diethyl-3-aminopimaleate (4.25 g, 18.5 mmol; from Step 1) was added followed by dimethylaminopyridine. After 1 hr. the solvent was removed under reduced pressure and the product purified by reverse phase chromatography (water/acetonitrile) to result in 4.1 g of a white solid: 1H NMR (d6-DMSO) δ 1.15 (t, 3H, J=7.3 Hz), 1.16 (t, 3H, J=8 Hz), 1.4 (m, 2H), 2.50 (t, 2H, J=7.1 Hz), 2.49 (m, 4H), 2.58 (t, 2H, J=7.1 Hz), 4.04 (m, 5H), 7.78 (s, 4H), 7.79 (d, 1H,J=12.4 Hz), 8.95 (bs, 2H), 9.15 (bs, 2H), 10.40 (s, 1H), MS (FAB) m/e 449.0 (M+H+).

Elemental Analysis Required for $C_{22}H_{32}N_4O_6.F_3.C_2O_2H.H_2O$: C 50.44, H 5.95, N 9.80. Found: C 50.33, H 6.02, N 9.67.

EXAMPLE 18

(±)-3-[[4-[[4-(aminoiminomethyl)phenyl]-amino]-1,4-dioxobutyl]amino-butyl]amino]heptanedioic acid

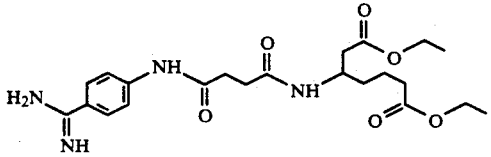

(±)-Diethyl-3-[[4-[[4-(aminoiminomethyl)phenyl]-amino]-1,4-dioxobutyl]amino]heptanedioate prepared in Example 17, Step 2 (700 mg) was added to water/acetonitrile (20 ml) followed by lithium hydroxide (100 mg) at 25° C. The mixture was stirred for 30 min. The course of the reaction was monitored by RPHPLC. After satisfactory monoester was formed the reaction was neutralized with TFA and purified by reverse phase chromatography (water/acetonitrile) to result in 550 mg of a white solid: 1H NMR (d6-DMSO) δ 1.4 (m, 2H), 2.50 (t, 2H, J=7.1 Hz), 2.49 (m, 4H), 2.58 (t, 2H, J=7.1 Hz), 4.02 (m, 1H), 7.77 (s, 4H), 7.78 (d, 1H, J=5.2 Hz), 8.90 (bs, 2H), 9.14 (bs, 2H), 10.39 (s, 1H); MS (FAB) m/e 393.4 (M+H+).

Elemental Analysis Required for $C_{18}H_{24}N_4O_6.F_3.C_2O_2H.H_2O$: C 46.60, H 5.04, N 10.87. Found: C 46.64, H 5.11, N 10.77.

EXAMPLE 19

Diethyl-3-[[4-[[4-(aminoiminomethyl)phenyl]amino]-1,4-dioxobutyl]amino]hexanedioate

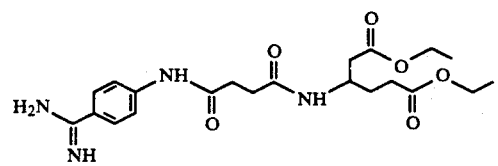

Step 1 Preparation of diethyl-3-aminoadipate

Diethyl-3-oxoadipate (10 g, 46 mmol) was added to methanol (225 ml) followed by ammonium formate (27.4 g, 460 mmol) and NaBH$_3$CN (2.7 g, 46 mmol) at 25° C. After 24 h the methanol was removed in vacuo to leave a white mass. Methylene chloride was added and the mixture filtered. The methylene chloride was evaporated resulting in an oil which was dissolved in 1N HCl (200 ml) and extracted with ether (100 ml). The ether layer was discarded and the aqueous layer was made basic using solid K$_2$CO$_3$. The product was extracted into methylene chloride dried over Na$_2$SO$_4$ and evaporated to give Diethyl-3-aminopimaleate (7.5 g). $^1$H NMR (d6-DMSO) δ 1.25 (t, 3H, J=8Hz), 1.26 (t, 3H, J=8Hz), 1.8 (m,2H), 1.55 (bs, 2H), 3.18 (m, 1H), 4.13 (q, 4H, J=8Hz), 4.15 (q, 4H, J=8Hz); MS (FAB) m/e 218.3 (M+H+).

Step 2 Preparation of diethyl-3-[[4-[[4-(aminoiminomethyl)phenyl]-amino]-1,4-dioxobutyl]amino]hexanedioate 4-[[4-(Aminoiminomethyl)phenyl]-amino]-4-oxobutanoic acid hydrochloride prepared in Example 1, Step 1 (5.0 g, 18.5 mmol) was added to dry DMF (250 ml) followed by N-methylmorpholine (1.8 g, 18.5 mmol) and isobutyl chloroformate (2.7 g, 17 mmol) at 25° C. The mixture was stirred for 5 min. Diethyl-3-aminoadipate (4.0 g, 18.5 mmol) was added followed by dimethylaminopyridine. After 1 hour the solvent was removed under reduced pressure and the product purified by reverse phase chromatography (water/acetonitrile) to result in 3.0 g of a white solid: $^1$H NMR (d6-DMSO) Δ 1.14 (t, 6H, J=7 Hz), 1.55 (m, 1H), 1.7 (m, 1H), 2.3 (m, 2H}, 2.57 (m, 2H), 2.67 (m, 2H), 4.02 (q, 4H, J=7 Hz), 4.03 (m, 1H), 7.79 (s, 4H), 7.99 (d, 1H, J=8.1 Hz), 9.06 (bs, 2H), 9.15 (bs, 2H), 10.22 (s, 1H); MS (FAB) m/e 435.2 (M+H+).

Elemental Analysis Required for C$_{21}$H$_{30}$N$_4$O$_6$.F$_3$C$_2$O$_2$H.H$_2$O: C 49.55, H 5.75, N 10.05. Found: C 49.36, H 5.42, N 9.92.

EXAMPLE 20

(±)-3-[[4-[[4-(Aminoiminomethyl)phenyl]amino]-1,4-dioxobutyl]amino]hexanedioic acid

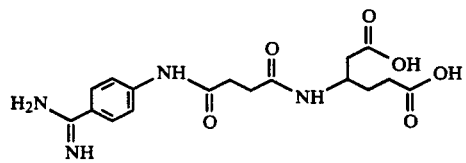

Diethyl-3-[[4-[[4-(aminoiminomethyl)phenyl]amino]-1,4-dioxobutyl]amino]hexanedioate (700 mg) prepared in Example 19, Step 2 was added to water/acetonitrile (20 ml) followed by lithium hydroxide (150 mg) at 25° C. The mixture was stirred for 30 min. The course of the reaction was monitored by RPHPLC. After satisfactory product was formed the reaction was neutralized with TFA and purified by reverse phase chromatography (water/acetonitrile) to result in 350 mg of a white solid: H NMR (d6-DMSO) δ 1.55 (m, 1H), 1.7 (m, 1H), 2.3 (m, 2H), 2.57 (m, 2H), 2.67 (m, 2H), 4.03 (m, 1H), 7.79 (s, 4H), 7.99 (d, 1H, J=8 Hz), 8.86 (bs, 2H), 9.17 (bs, 2H), 10.2 (s, 1H); MS (FAB) m/e 379.2 (M+H+).

Elemental Analysis Required for C$_{17}$H$_{22}$N$_4$O$_6$.F$_3$C$_2$O$_2$H.H$_2$O: C 45.51, H 4.79, N 11.18. Found: C 45.57, H 4.49, N 11.18.

EXAMPLE 21

3S-[[4-[[4-(aminoiminomethyl)phenyl]-amino]-1,4-dioxobutyl]amino]-4-(hydroxyamino)-4-oxobutanoic acid

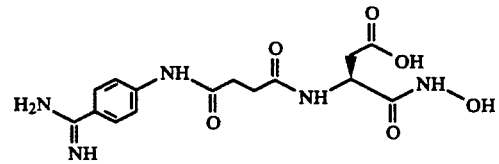

Step 1 Preparation of benzyl-3-amino-4-oxo-(n-hydroxylamino)-(3S)-butyrate

N-tBoc-L-aspartic acid, B-benzyl ester (10 g, 3.0 mmol) was dissolved in 100 ml of methylene chloride and added dropwise over a period of 10 min. to a solution of DCC (6.3 g, 3.0 mmol) in methylene chloride (20 ml) at 25° C. under a N$_2$ atmosphere. After the solution was stirred for 0.5 h, trimethylsilyl hydroxylamine (3.0 g, 3 mmol) was added to the reaction mixture followed by DMAP (0.5 g). After the reaction was complete ether was added to the mixture and the DCU was filtered through a pad of celite. The solution was concentrated to give an oil which was dissolved in dioxane. To that solution was added 4N HCl in dioxane (20 ml). The product was isolated by filtration to give the desired product (4g) as its hydrochloride salt. 1 H NMR (d6-DMSO) δ 2.95 (m, 2H, ), 4.36 (m, 1H), 5.12 (d, 2H, J=7 Hz), 7.37 (bs, 5H).

Step 2 3S-[[4-[[4-(aminoiminomethyl)phenyl]-amino]-1,4-dioxobutyl]amino]-4-(hydroxyamino)-4-oxobutanoic acid 4-[[4-(aminoiminomethyl)phenyl]-amino]-4-oxobutanoic acid hydrochloride prepared in Example 1, Step 1 (5.0 g, 18.5 mmol) was added to dry DMF (250 ml) followed by N-methylmorpholine (1.8 g, 18.5 mmol) and isobutyl chloroformate (2.7 g, 18.5 mmol) at 25° C. The mixture was stirred for 5 min. Benzyl-3S-amino-4-oxo-4-(n-hydroxylamino)butyrate hydrochloride (3.0 g, 18.5 mmol; from Step 1) was added followed by dimethylaminopyridine. After 1 h the solvent was removed under reduced pressure and the product purified by reverse phase chromatography (water/acetonitrile) to result in 2.1 g of a white solid. A portion of this material was then subjected to saponification conditions as previously described and purified by reverse phase chromatography (water/acetonitrile) to result in 225 mg of a white solid: $^1$H NMR (d6-DMSO) δ 2.44 (m, 3H), 2.60 (m, 2H), 2.4 (m, 1H), 4.49 (m, 1H), 6.98 (d, 1H, J=8.0 Hz), 7.78 (s, 4H), 8.62 (d, 1H, J=7.7 Hz), 8.94 (bs, 2H), 9.16 (bs, 2H), 10.20 (s, 1H); MS (FAB) m/e 348.1 (M+H+).

Elemental Analysis Required for C$_{15}$H$_{19}$N$_5$O$_5$.F$_3$C$_2$O$_2$H.H$_2$O: C 44.25, H 3.90, N 15.18. Found: C 44.13, H 4.07, N 13.68.

EXAMPLE 22

3R-[[4-[[4-(aminoiminomethyl)phenyl]-amino]-1,4-dioxobutyl]amino]-4-azidobutanoic acid

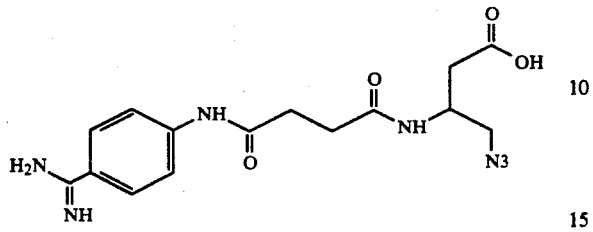

Step 1 Preparation of Benzyl-3-amino-4-azido butyrate

The mesylate (27 g, 64 mmol) from Step 1, Example 16 was added to dry DMF followed by NaN3 (12.6 g, 194 mmol), TDA-1 (0.5 g) DMAP (1.0 g) and heated at 70° C. for 2-3 h. After complete reaction water was added and the product was extracted with ether (2×150 ml). The ether extracts were washed with water, then dried over MgSO4, and the solvent evaporated to give benzyl-3-N-tBoc-amino-4-azido-(3S)-butyrate (20 g).

The crude Benzyl-3-N-tBoc-amino-4-azido-(3S)-butyrate was dissolved in dioxane (100 ml) and to this solution 4N HCl in dioxane was added. After 6 h the dioxane was removed in vacuo to leave an oil to give Benzyl-3-amino-4-azido-(3S)-butyrate hydrochloride (11 g). 1H NMR (d6-DMSO) d 2.9 (dd, 2H, J=5.65, 15 Hz), 3.83 (bs, 2H), 5.16 (s, 2H), 7.36 (bs, 5H); H); MS (FAB) m/e 235.1 (M+H+).

Step 2 Preparation of 3R-[[4-[[4-(aminoiminomethyl)phenyl]-amino]-1,4-dioxobutyl]amino]-4-azidobutanoic acid 4-[[4-(aminoiminomethyl)phenyl]-amino]-4-oxobutanoic acid hydrochloride prepared in Example 1, Step 1 (4.6 g, 18.5 mmol) was added to dry DMF (250 ml) followed by N-methylmorpholine (1.8 g, 18.5 mmol) and isobutyl chloroformate (2.8 g, 17 mmol) at 25° C. The mixture was stirred for 5 min. Benzyl-3-amino-4-azido-(3S)-butyrate hydrochloride (1 eq; from Step 1, Example 22) was added followed by dimethylaminopyridine. After 1 h the solvent was removed under reduced pressure and the product purified by reverse phase chromatography (water/acetonitrile) to result in 3.0 g of a white solid. A portion (750 mg) of the benzyl ester was subjected to the saponification conditions as previously described and purified by reverse phase chromatography (water/acetonitrile) to result in 340 mg of a white solid: 1H NMR (d6-DMSO) Δ 2.44 (m, 4H), 2.6 (m, 2H), 3.35 (bs, 2H), 4.18 (m, 1H), 7.78 (s, 4H), 8.1 (d, 1H,J=8 Hz), 8.27 (bs, 2H), 9.15 (bs, 2H), 10.40 (s, 1H); MS (FAB) m/e 362.1 (M+H+).

Elemental Analysis Required for $C_{15}H_{19}N_7O_4 \cdot F_3C_2O_2H \cdot H_2O$: C 42.63, H 4.18, N 20.48. Found: C 42.49, H 4.06, N 20.06.

EXAMPLE 23

Dimethyl [[[4-[[4-(aminoiminomethyl)phenyl]amino]-,4-dioxobutyl]amino]propanedioate

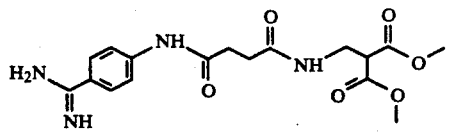

Step 1 Preparation of Dimethyl-2-(aminomethyl) malonate

Dimethyl malonate (10 g, 75.8 mmol) was added to DMF/water (70:30), K2CO3 (15 g, 100 mmol), PTC (1 g), NaI (1 g), and tert-butyl bromoacetate (14.7 g, 75.8 mmol) at 25° C. The mixture was vigorously stirred for 24 h. After this time water (250 ml) was added and the product was extracted with ether and dried over MgSO4. The oil which resulted after concentrating the solution was dissolved in methylene chloride (80 ml) and TFA (20 ml) and the resulting mixture was stirred for 3-6 hr. After this time the solution was concentrated in vacuo to give a viscous oil (8 g). A portion of this oil (5 g, 26.3 mmol) was dissolved in DMF (50 ml). Diphenyl phosphorazide (7.5 g, 26.3 mmol) was added and the resulting mixture was cooled to 0° C. Triethylamine (2.7 g, 26.3 mmol) was added and the solution stirred for 2 h. After this time water was added (200 ml) and the acyl azide extracted into ether, dried over MgSO4 and the solvent removed. The oil was dissolved in dioxane followed by the addition of 4N HCl in dioxane (10 ml). The product a white solid soon separated out as its hydrochloride salt (3 g). 1H NMR (d6-DMSO) δ 3.25 (m, 2H), 3.70 (s, 3H), 4.0 (t, 1H, J=7 Hz), 8.4 (bs, 2H); MS (FAB) m/e 162.1 (M+H+), 145.2, 133.3.

Step 2 Preparation of Dimethyl [[[4-[[4-(aminoiminomethyl)phenyl]-amino]-1,4dioxobutyl]amino]propanedioate 4-[[4-(Aminoiminomethyl)phenyl]-amino]-4-oxobutanoic acid hydrochloride prepared in Example 1, Step 1 (5.0 g, 18.5 mmol) was added to dry DMF (250 ml) followed by N-methylmorpholine (1.7 g, 18.5 mmol) and isobutyl chloroformate (2.8 g, 17 mmol) at 25° C. The mixture was stirred for 5 min. Dimethyl-2-(aminomethyl) malonate (from Step 1; 1 eq) was added followed by dimethylaminopyridine. After 1 h the solvent was removed under reduced pressure and the product purified by reverse phase chromatography (water/acetonitrile) to result in 2.0 g of a white solid: 1H NMR (d6-DMSO) δ 2.57 (m, 2H), 2.07 (m, 2H), 3.47 (m, 2H), 3.5 (s, 6H), 3.51 (m, 1H), 7.79 (s, 4H), 8.1 (t, 1H, J=7 Hz), 8.7 (bs, 2H), 9.09 (bs, 2H), 10.32 (s, 1H); MS (FAB) m/e 379.0 (M+H+).

Elemental Analysis Required for $C_{17}H_{22}N_4O_6 \cdot H_2O$: C 45.50, H 4.72, N 11.18. Found: C 45.20, H 4.66, N 11.17.

EXAMPLE 24

[[[4-[[4-(aminoiminomethyl)phenyl]-amino]-1,4-dioxobutyl]amino]propanedioic acid

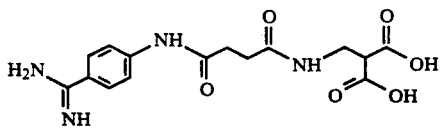

Dimethyl [[[4-[[4-(aminoiminomethyl)phenyl]amino]-1,4-dioxobutyl]amino]propanedioate prepared in Example 23, Step 2 (500 mg) was added to water/acetonitrile (20 ml) followed by lithium hydroxide (100 mg) at 25° C. The mixture was stirred for 30 min. The course of the reaction was monitored by RPHPLC. After satisfactory product was formed the reaction was neutralized with TFA and purified by reverse phase chromatography (water/acetonitrile) to result in 350 mg of a white solid: $^1$H NMR (d$_6$-DMSO) δ 2.41 (m, 2H), 2.57 (m, 2H), 3.47 (m, 2H), 3.5 (s, 6H), 3.51 (m, 1H), 7.79 (s, 4H), 8.1 (t, 1H, J=6.1 Hz), 3.35 (m,1H), 3.4 (m,2H), 7.78 (s, 4H), 8.02 (m, 1H), 8.87 (bs, 2H), 9.15 (bs, 2H), 10.39 (s, 1H); MS (FAB) m/e 350.0 (M+H+).

Elemental Analysis Required for $C_{15}H_{18}N_4O_6 \cdot F_3 \cdot C_2O_2H \cdot H_2O$: C 44.32, H 4.32, N 13.66. Found: C 44.72, H 4.72, N 13.06.

EXAMPLE 25

Methyl-3±-[[4-[[4-(aminoiminomethyl)phenyl]amino]-1,4-dioxobutyl]amino]-4-methoxyethylbutyrate

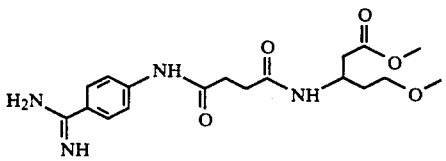

Step 1 Preparation of methyl-5-methoxy-3-aminovalerate

Methyl-5-methoxy-3-aminovalerate (10 g, 62.5 mmol) was added to methanol (200 ml) followed by ammonium formate (39.4 g, 620 mmol) and NaBH$_3$CN (3.9 g, 46 mmol) at 25° C. After 24 h the methanol was removed in vacuo to leave a white mass. Methylene chloride was added and the mixture filtered. The methylene chloride was evaporated resulting in an oil which was dissolved in 1N HCl (200 ml) and extracted with ether (100 ml). The ether layer was discarded and the aqueous layer was made basic using solid K$_2$CO$_3$. The product was extracted into methylene chloride dried over Na$_2$SO$_4$ and evaporated to give methyl-5-methoxy-3-aminovalerate (7.5 g). $^1$H NMR (d6-DMSO) δ 1.66 (m, 2H), 4.1 (m, 1H), 7.75 (5,4H), 7.85 (d, 1H, J=8 Hz); 9.0 (bs, 2H), 9.17 (bs, 2H), 2.4 (m, 4H), 2.6 (m, 2H), 3.33 (s, 3H), 3.29 (m, 2H), 3.55 (s, 3H); MS (FAB) m/e 161.2 (M+H+).

Step 2 Preparation of methyl-3-[[4-[[4-(aminoiminomethyl)phenyl]-amino]-1,4-dioxobutyl]amino]-4-methoxyethylbutyrate 4-[[4-(Aminoiminomethyl)phenyl]-amino]-4-oxobutanoic acid hydrochloride prepared in Example 1, Step 1 (5.0 g, 18.5 mmol) was added to dry DMF (250 ml) followed by N-methylmorpholine (1.7 g, 18.5 mmol) and isobutyl chloroformate (2.8 g, 17 mmol) at 25° C. The mixture was stirred for 5 min. Methyl-5-methoxy-3-aminovalerate (3.0 g, 18.5 mmol) was added followed by dimethylaminopyridine. After 1 h the solvent was removed under reduced pressure and the product purified by reverse phase chromatography (water/acetonitrile) to result in 2.8 g of a white solid: $^1$H NMR (d$_6$-DMSO) δ 1.74 (m, 2H), 2.4 (m, 4H), 2.6 (m, 2H), 3.16 (s, 3H), 3.33 (m, 2H), 3.56 (s, 3H), 4.12 (m,1H), 7.78 (s, 4H), 7.81 (d, 1H,J=8.5 Hz), 9.02 (bs, 2H), 9.15 (bs, 2H), 10.40 (s, 1H); MS (FAB) m/e 379.5 (M+H+).

Elemental Analysis Required for $C_{18}H_{26}N_4O_5 \cdot F_3 \cdot C_2O_2H \cdot H_2O$: C 48.78, H 5.49, N 11.38. Found: C 48.35, H 5.55, N 10.32.

EXAMPLE 26

3-[[4-[[4-(aminoiminomethyl)phenyl]-amino]-1,4-dioxobutyl]amino]-4-methoxyethylbutyric acid

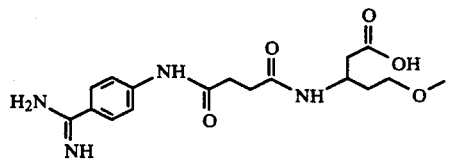

Methyl-3-[[4-[[4-(aminoiminomethyl)phenyl]amino]-1,4-dioxobutyl]amino]-4-methoxyethylbutyrate prepared in Example 25, Step 2 (500 mg) was added to water/acetonitrile (20 ml) followed by lithium hydroxide (100 mg) at 25° C. The mixture was stirred for 30 min. The course of the reaction was monitored by RPHPLC. After satisfactory product was formed the reaction was neutralized with TFA and purified by reverse phase chromatography (water/acetonitrile) to result in 450 mg of a white solid: $^1$H NMR (d$_6$-DMSO) δ 1.74 (m, 2H), 2.4 (m, 4H), 2.6 (m, 2H), 3.16 (s, 3H), 3.33 (m, 2H), 4.12 (m,1H), 7.78 (s, 4H), 7.81 (d, 1H, J=8.5 Hz), 9.02 (bs, 2H), 9.15 (bs, 2H), 10.40 (s, 1H); MS (FAB) m/e 365.4 (M+H+).

Elemental Analysis Required for $C_{17}H_{24}N_4O_5 \cdot F_3 \cdot C_2O_2H \cdot H_2O$: C 46.82, H 5.33, N 11.49, Found: C 46.68, H 5.13, N 11.05.

EXAMPLE 27

Dimethyl 2-[1-[[4-[[4-(aminoiminomethyl)phenyl]-amino]-1,4-dioxobutyl]amino]ethyl]-succinate

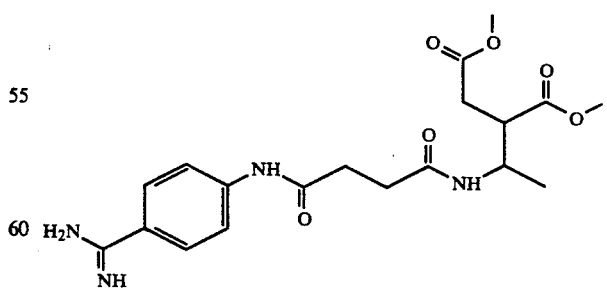

Step 1 Preparation of dimethyl-2-(aminoethyl) succinate

Dimethyl acetylsuccinate (10 g, 53 mmol) was added to methanol (200 ml) followed by ammonium formate (34 g, 530 mmol) and NaBH₃CM (3.4 g, 53 mmol) at 25° C. After 24 h the methanol was removed in vacuo to leave a white mass. Methylene chloride was added and the mixture filtered. The methylene chloride was evaporated resulting in an oil which was dissolved in 1N HCl (200 ml) and extracted with ether (100 ml). The ether layer was discarded and the aqueous layer was made basic using solid K₂CO₃. The product was extracted into methylene chloride dried over Na₂SO₄ and evaporated to give dimethyl-2-(aminoethyl) succinate (6 g). 1 H NMR (d6-DMSO) δ 0.97 (d, 3H, J=7.1 Hz), 2.66 (m, 2H), 3.05 (m, 1H), 3.56 (s, 3H), 3.60 (s, 3H), 4.15 (m, 1H); MS (FAB) m/e 190.2 (M+H+), 158.2, 141.2.

Step 2 Preparation of dimethyl-(2-[1-[[4-[[4-(aminoiminomethyl)phenyl]-amino]-1,4-dioxobutyl]amino]ethyl]-succinate 4-[[4-(aminoiminomethyl)phenyl]-amino]-4 oxobutanoic acid hydrochloride prepared in Example 1, Step 1 (5.0 g, 18.5 mmol) was added to dry DMF (250 ml) followed by N-methylmorpholine (1.8 g, 18.5 mmol) and isobutyl chloroformate (2.7 g, 18.5 mmol) at 25° C. The mixture was stirred for 5 minutes. Dimethyl-(2-aminoethyl) succinate (3.5 g, 18.5 mmol) was added followed by dimethylaminopyridine. After 1 h the solvent was removed under reduced pressure and the product purified by reverse phase chromatography (water/acetonitrile) to result in 2.1 g of a white solid. ¹H NMR (d6-DMSO) δ 0.98 (d, 3H, J=7.1 Hz), 2.44 (m,2H), 2.55 (m,4H), 3.1 (m, 1H), 3.55 (s, 3H), 3.58 (s, 3H), 4.15 (m, 1H), 7.78 (s, 4H), 7.92 (d, 1H, J=7.7 Hz), 8.84 (bs, 2H), 9.16 (bs, 2H), 10.20 (s, 1H); MS (FAB) m/e 407.2 (M+H+).

Elemental Analysis Required for C₁₉H₂₆N₄O₆.F₃.C₂O₂H.H₂O: C 48.46, H 5.19, N 10.76. Found: C 48.83, H 5.33, N 10.75.

EXAMPLE 28

Ethyl β-[[4-[[4-(aminoiminomethyl)phenyl]amino]-1,4-dioxobutyl]amino]cyclopropanepropanoate

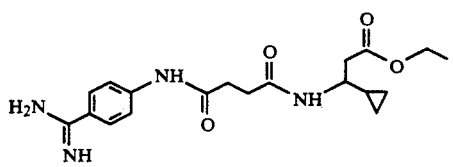

The title compound was prepared in the manner of Example 1 substituting ethyl 3-amino-3-cyclopropyl-propanoate for D,L-3-amino-3-phenylpropionic acid. The product was purified by reverse phase HPLC using the conditions of Example 1 to afford the title compound. The product was verified by ¹³C NMR (CD₃OD) δ 2.5, 3.2, 13.6, 15.0, 30.8, 32.5, 40.1, 51.4, 60.8, 119.8, 122.7, 129.2, 144.9, 166.8, 172.1, 172.6, 173.0, Chemical ionization mass spectrometry (MH+)=375.

EXAMPLE 29

β-[[4-[[4-(Aminoiminomethyl)phenyl]amino]-1,4-dioxobutyl]amino]cyclopropanepropanoic acid

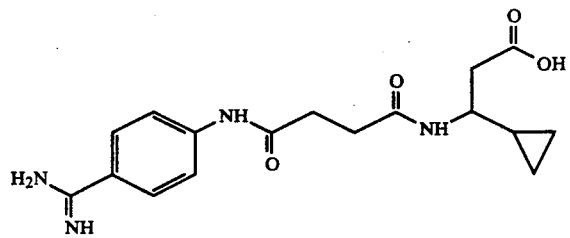

Porcine liver esterase (200 μL, Sigma, 11 mg/mL in 3.2 M (NH₄)₂SO₄ at pH=8) was added to the final product of Example 28 in 20mL of 0.1 M phosphate buffer (pH=7.4). After 20 h at 23° C., the reaction mixture was concentrated in vacuo. The residue was dissolved in 1N HCl (3 mL) and subsequently diluted with acetonitrile (5 mL) followed by immediate purification by reverse phase HPLC using the conditions of Example 1 to afford 23.0 mg (83%) of the title compound. The product was verified by ¹³C NMR (CD₃OD) δ 1.8, 2.6, 15.0, 30.3, 31.8, 39.1, 50.6, 119.2, 122.1, 128.6, 144.3, 166.8, 172.0, 172.4, 173.4; Fast Atom Bombardment mass spectrometry (MH+)=347.

EXAMPLE 30

Ethyl 3-[[4-[[4-(aminoiminomethyl)phenyl]amino)-1,4-dioxobutyl]amino]-5-hexenoate

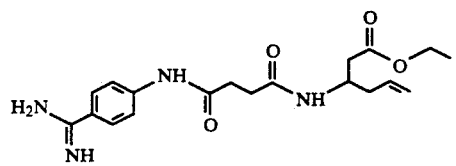

The title compound was prepared in the manner of Example 1 substituting ethyl 3-amino-5-hexenoate for D,L-3-amino-3-phenylpropionic acid. The product was purified by reverse phase HPLC using the conditions of Example 1 to afford the title compound. The product was verified by CNMR (CD₃OD) δ 12.6, 29.8, 31.3, 37.9, 45.9, 59.9, 116.5, 118.7, 121.5, 128.1, 133.4, 143.7, 165.6, 171.1, 171.6, 172.2; Fast Atom Bombardment Mass Spectrometry (MH+)=375.

EXAMPLE 31

3-[[4-[[4-(aminoiminomethyl)phenyl]amino]-1,4-dioxobutyl]amino]-5-hexenoic acid

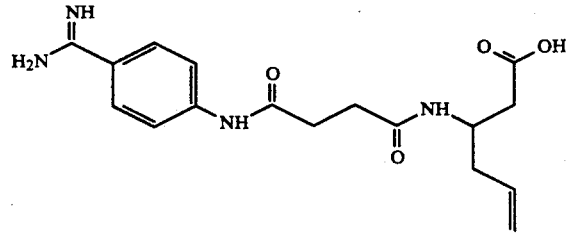

The title compound was prepared by treating the final product of the previous example with porcine liver esterase in the manner of Example 29. The product was purified by reverse phase HPLC using the conditions of Example 1 to afford the title compound. The product was verified by $^{13}$C NMR (CD$_3$OD) δ 31.3, 32.8, 39.0, 39.2, 47.0, 117.8, 120.2, 123.1, 129.5, 135.1, 145.2, 165.6, 173.0, 173.6, 174.4; Fast Atom Bombardment Mass Spectrometry (MH+)=347.

Elemental Analysis Required for C$_{17}$H$_{22}$N$_4$O$_4$.1.0 CF$_3$CO$_2$H.0.6H$_2$O: C 48.43, H 5.18, N 11.89. Found: C 48.14, H 4.86, N 11.72.

EXAMPLE 32

Ethyl 3-[[4-[[4-(aminoiminomethyl)phenyl]amino]-1,4-dioxobutyl]amino]4-pentenoate

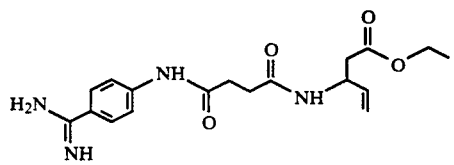

The title compound was prepared in the manner of Example 1 substituting ethyl 3-amino-4-pentenoate for D,L-3-amino-3-phenylpropionic acid. The product was purified by reverse phase HPLC using the conditions of to afford the title compound. The product was verified by $^{13}$C NMR (CD$_3$OD): δ 12.8, 29.5, 31.0, 47.5, 59.5, 69.3, 113.8, 118.2, 121.1, 128.2, 136.5, 143.7, 165.9, 169.9, 170.9, 171.0; Fast Atom Bombardment Mass Spectrometry (MH+)=361.

Anal. Calcd for C$_{18}$H$_{24}$N$_4$O$_4$.1.0 CF$_3$CO$_2$H.0.5 H$_2$O: C 49.69, H 5.42, N 11.59. Found: C 49.93, H 5.30, N 11.39.

EXAMPLE 33

3-[[4-[[4-(aminoiminomethyl)phenyl]amino]-1,4-dioxobutyl]amino]4-pentenoic acid

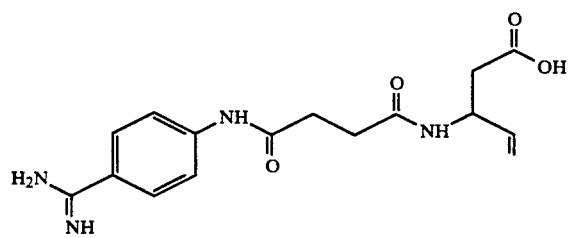

The title compound was prepared by treating the final product of the previous example with porcine liver esterase in the manner of Example 29. The product was purified by reverse phase HPLC using the conditions of Example 1 to afford the title compound. The product was verified by $^{13}$C NMR (CD$_3$OD) δ 30.0, 31.3, 38.2, 47.9, 114.0, 118.9, 119.0, 128.1, 136.3, 165.9, 171.8, 172.1, 173.2; Fast Atom Bombardment Mass Spectrometry (MH+)=333.

Anal. Calcd. for C$_{16}$H$_{20}$N$_4$O$_4$.1.0 CF$_3$CO$_2$H.1.45 H$_2$O: C 45.76, H 5.10, N 11.86. Found: C 45.37, H 4.74, N 12.29.

EXAMPLE 34

Ethyl β-[[4-[[4-(aminoiminomethyl)phenyl]amino]-1,4-dioxobutyl]amino]benzenebutanoate

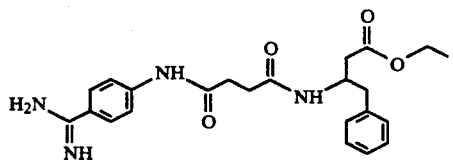

The title compound was prepared in the manner of Example 1 substituting ethyl 3-amino-4-phenylbutanoate for D,L-3-amino-3-phenylpropionic acid. The product was purified by reverse phase HPLC using the conditions of Example 1 to afford the title compound. The product was verified by $^{13}$C NMR (CD$_3$OD) δ 13.6, 30.8, 32.2, 38.8, 40.4, 48.7, 60.8 119.7, 122.7, 126.6, 128.5, 129.0, 129.5, 138.4, 144.8, 166.1, 171.2, 172.0, 172.5; Fast Atom Bombardment Mass Spectrometry (MH+)=425.

Anal. Calcd. for C$_{23}$H$_{28}$N$_4$O$_4$.1.0 CF$_3$CO$_2$H.0.5 H$_2$O: C 54.84, H 5.52, N 10.23. Found: C 54.78, H 5.40, N 10.20.

EXAMPLE 35

β-[[4-[[4-(aminoiminomethyl)phenyl]amino]-1,4-dioxobutyl]amino]benzenebutanoic acid

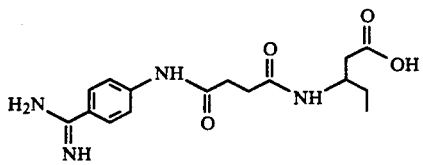

The title compound was prepared by treating the final product of the previous example with porcine liver esterase in the manner of Example 29. The product was purified by reverse phase HPLC using the conditions of Example 1 to afford the title compound. The product was verified by $^{13}$C NMR (CD$_3$OD) δ 30.2, 31.7, 37.8, 39.6, 47.1, 119.2, 122.1, 126.1, 128.6, 129.0, 138.0, 144.3, 166.2, 172.0, 172.5, 173.2; Fast Atom Bombardment Mass Spectrometry (MH+)=397.

Anal. Calcd. for C$_{21}$H$_{24}$N$_4$O$_4$.1.4 CF$_3$CO$_2$H: C 51.41, H 4.60, N 10.08. Found: C 51.75, H 4.64, N 10.43.

EXAMPLE 36

Ethyl 3-[[4-[[4-(aminoiminomethyl)phenyl]amino]-1,4-dioxobutyl]amino]-5-(trimethylsilyl)-4-pentynoate

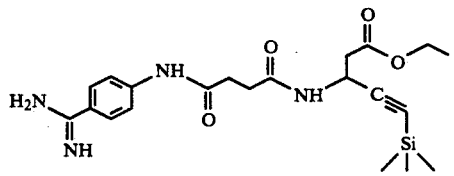

The title compound was prepared in the manner of Example 1 substituting ethyl 5-(trimethylsilyl)-4-pentynoate for D,L-3-amino-3-phenylpropionic acid. The product was purified by reverse phase HPLC using the conditions of Example 1 to afford the title compound The product was verified by $^{13}$C NMR (CD$_3$OD) δ −1.5, 13.2, 30.0, 31.4, 38.6, 40.1, 60.6, 87.0, 103.3, 119.2, 122.0, 128.6, 144.2, 166.1, 170.0, 172.0, 172.1; Fast Atom Bombardment Mass Spectrometry (MH+)=431.

Anal. Calcd. for C$_{21}$H$_{30}$N$_4$O$_4$Si.1.3 CF$_3$CO$_2$H: C 48.97, H 5.45, N 9.68. Found: C 48.68, H 5.41, N 9.71.

EXAMPLE 37

3-[[4-[[4-(aminoiminomethyl)phenyl]amino]-1,4-dioxobutyl]aminol]-5-(trimethylsilyl)-4-pentynoic acid

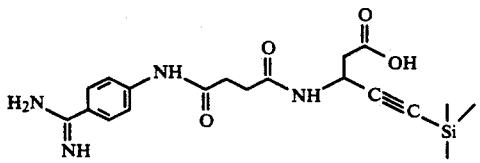

The title compound was prepared by treating the final product of the previous example with porcine liver esterase in the manner of Example 29. The product was purified by reverse phase HPLC using the conditions of Example 1 to afford the title compound. The product was verified by $^{13}$C NMR (CD$_3$OD) δ −0.6, 30.8, 32.3, 39.4, 40.7, 87.6, 104.5, 120.1, 123.0, 129.5, 145.2, 166.2, 172.8, 172.9, 173.0; Fast Atom Bombardment Mass Spectrometry (MH+)=403

Anal. Calcd. for C$_{19}$H$_{26}$N$_4$O$_4$Si.1.4 CF$_3$CO$_2$H: C 45.66, H 4.82, N 9.77. Found: C 45.84, H 4.92, N 9.86.

EXAMPLE 38

Ethyl 3-[[4-[[4-(aminoiminomethyl)phenyl]amino]-1,4-dioxobutyl]amino]-4-pentynoate

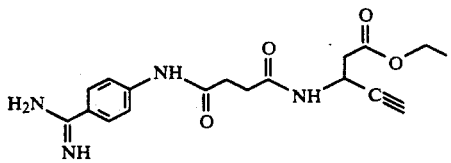

The title compound was prepared in the manner of Example 1 substituting ethyl 3-amino-4-pentynoate for D,L-3-amino-3-phenylpropionic acid. The product was purified by reverse phase HPLC using the conditions of to afford the title compound. The product was verified by $^{13}$C NMR (CD3OD) δ 13.6, 30.3, 31.9, 38.1, 40.4, 61.0, 71.9, 82.0, 119.6, 122.5, 129.1, 144.8, 166.5, 170.3, 172.1, 172.2; Fast Atom Bombardment Mass Spectrometry (MH+)=359.

Anal. Calcd. for C$_{16}$H$_{18}$N$_4$O$_4$.1.5 CF$_3$CO$_2$H.0.65 H$_2$O: C 44.48, H 4.09, N 10.92. Found: C 44.05, H 4.19, N 11.38.

EXAMPLE 39

(±)-3-[[4-[[4-(aminoiminomethyl)phenyl]amino]-1,4-dioxobutyl]amino]-4-pentynoic acid

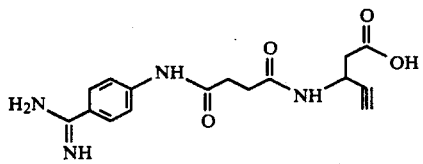

The title Compound was prepared by treating the final product of the previous example with porcine liver esterase in the manner of Example 29. The product was purified by reverse phase HPLC using the conditions of Example 1 to afford the title compound. The product was verified by C NMR (CD$_3$OD) Δ 29.9, 31.4, 37.7, 39.5, 71.1, 81.5, 119.2, 122.1, 128.3, 144.2, 166.2, 171.8, 172.0, 172.1; Fast Atom Bombardment Mass Spectrometry (MH+)=331.

Anal. Calcd. for C$_{16}$H$_{18}$N$_4$O$_4$.1.5 CF$_3$CO$_2$H.0.65 H$_2$O: C 44.48, H 4.09, N 10.92. Found: C 44.05, H 4.19, N 11.38.

EXAMPLE 40

Phenylmethyl 3S-[[4-[[4-(aminoiminomethyl)phenyl]amino]-1, 4-dioxobutyl]aminol-4-(methoxyimino)butanoate

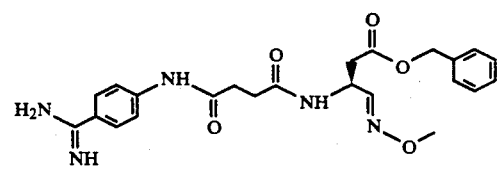

The title compound was prepared in the manner of Example 1 substituting phenylmethyl 3(S)-amino-4-(methoxyimino)butanoate for D, L,-3-amino-3-phenylpropionic acid. The product was purified by reverse phase HPLC using the conditions of Example 1 to afford the title compound. The product was verified by $^{13}$C NMR (CD$_3$OD) δ 30.0, 31.5, 36.3, 43.5, 46.2, 61.2, 61.7, 66.7, 119.2, 122.1, 127.8, 128.1, 128.6, 136.0, 144.3, 148.0, 150.2, 166.1, 170.5, 172.0, 172.8; Fast Atom Bombardment Mass Spectrometry (MH+)=454.

EXAMPLE 41

3S-[[4-[[4-[aminoiminomethyl)phenyl]amino]-1,4-dioxobutyl]amino]-4-(methoxyimino)butanoic acid

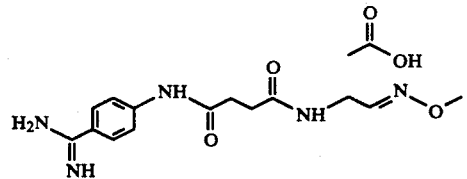

The title compound was prepared by treating the final product of Example 40 with porcine liver esterase in the manner of Example 29. The product was purified by reverse phase HPLC using the conditions of example i to afford the title compound. The product was verified by C NMR (CD$_3$OD) Δ 30.2, 31.8, 36.2, 47.4, 61.0, 119.2, 122.4, 128.8, 144.6, 148.8, 166.0, 171.8, 172.1, 172.4; Fast Atom Bombardment Mass Spectrometry (MH+)=364.

Anal. Calcd. for C$_{16}$H$_{21}$N$_5$O$_5$.1.25 CF$_3$CO$_2$H.0.5 H$_2$O: C 43.15, H 4.55, N 13.60. Found: C 43.26, H 4.19, N 13.36.

EXAMPLE 42

Ethyl 3-[[4-[[4-(aminoiminomethyl)-3-chlorophenyl]amino]-1,4-dioxobutyl]amino]butanoate

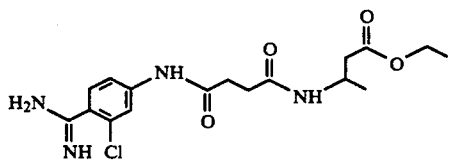

Step 1 Preparation of 4-[[4-(aminoiminomethyl)-3-chlorophenyl]amino]-4-oxobutanoic acid hydrochloride To a mixture of 4-amino-2-chlorobenzonitrile (3.05 g, 20.0 mmol), diisopropylamine (5.0 mL, 30.0 mmol), and methylene chloride (20 mL) at 0° C. under nitrogen was added 3-carbomethoxypropionyl chloride (4.50 g, 30.0 mmol) dropwise over 3 min. After 10 min at 0° C., the reaction mixture was allowed to warm up to 23° C. After 2 h, the reaction mixture was concentrated in vacuo, diluted with ethyl acetate (150 mL), washed with 1N KHSO$_4$ (1×80 mL), brine (1×80 mL), dried (Na$_2$SO$_4$), and concentrated in vacuo. The residue was diluted with ether (80 mL), filtered, and concentrated in vacuo. This procedure afforded material (4.5 g, 85%) of sufficient purity to be taken on to the next step without further purification.

The ester (4.0 g, 15 mmol) was hydrolyzed by treating with 1N NaOH: methanol (15 mL:60 mL) for 45 min. The reaction was concentrated in vacuo, diluted with 5% NaHCO$_3$ (150 mL), and extracted with ethyl acetate (60 mL). The aqueous layer was acidified (pH1-2) with 1N KHSO$_4$ and extracted with ethyl acetate (2×100 mL). After drying (MgSO$_4$), the ethyl acetate was removed in vacuo to afford the free acid (3.1 g, 82%).

Hydrogen sulfide was bubbled through a solution of 4.0 g (15.9 mmol) of the above acid in pyridine:triethyl amine (24 mL:2.4 mL) for 5 minutes at 23° C. After 24 h at 23° C. in an enclosed flask, the reaction mixture was concentrated under a steady stream of nitrogen. The residue was diluted with ethyl acetate (300 mL), washed with KHSO$_4$ (1N, 2×100 mL), brine (1×50 mL), and dried (Na$_2$SO$_4$). Concentration in vacuo afforded a quantitative mass recovery of the thioamide.

The thioamide (4.53 g, 15.8 mmol) was dissolved in a solution of acetone:iodomethane (28 mL:2 mL). The reaction mixture was warmed to achieve reflux for 40 minutes. Concentration in vacuo followed by trituration with ether and filtration afforded a quantitative yield of the HI salt.

A solution of thioimidate (15.8 mmol) and ammonium acetate (1.83 g, 23.7 mmol) in methanol (10 mL) was warmed to achieve reflux for 4 h. After cooling to 23° C., the reaction mixture was concentrated under a steady stream of nitrogen in the hood. The residue was dissolved in H$_2$O (20 mL) and diluted with acetone (80 mL) to afford the zwitter-ion (2.53 g, 59.4%). The hydrochloride salt was formed by treatment with 6N HCl in dioxane (40 mL) for 1 h at 23° C. Concentration in vacuo afforded the hydrochloride salt which was azeotroped with benzene prior to use.

Step 2 Ethyl 3-[[4-[[4-(aminoiminomethyl)-3-chlorophenyl]amino]-1,4-dioxobutyl]amino]butanoate The title compound was prepared in the manner of Example 1 substituting ethyl 3-aminobutanoate for D,L-3-amino-3-phenylpropionic acid and using the acid prepared in Step 1 of Example 42. The product was purified by reverse phase HPLC using the conditions of Example 1 to afford the title compound. The product was verified by $^{13}$C NMR (CD$_3$OD) δ 15.5, 21.5, 31.3, 33.0, 43.2, 61.2, 118.5, 120.5, 124.7, 132.0, 132.3, 144.6, 144.8, 165.7, 171.6, 172.9; Chemical Ionization Mass Spectrometry (MH+)=383.

EXAMPLE 43

3-[[4-[[4-(aminoiminomethyl)-3-chlorophenyl]amino]-1,4-dioxobutyl]amino]butanoic acid

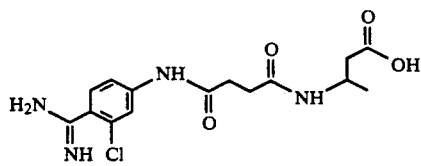

The title compound was prepared by treating the final product of the previous example with porcine liver esterase in the manner of Example 29. The product was purified by reverse phase HPLC using the conditions of example 1 to afford the title compound. The product was verified by $^{13}$C NMR (CD3OD) δ 18.6, 29.8, 31.3, 39.8, 42.0, 117.2, 119.9, 123.5, 129.7, 131.4, 143.5, 166.0, 172.0, 172.1, 173.1; Fast Atom Bombardment Mass Spectrometry (MH+)=355.

Anal. Calcd. for C$_{15}$H$_{19}$N$_4$O$_4$Cl.1.0 CF$_3$CO$_2$H.1.0 H$_2$O: C 41.94, H 4.55, N 11.51. Found: C 41.63, H 4.23, N 11.89.

EXAMPLE 44

3S - [[4-(aminoiminoethyl)phenyl]amino]-1,4-dioxobutyl]amino]-4-(methoxymethylamino)4-oxobutanoic acid

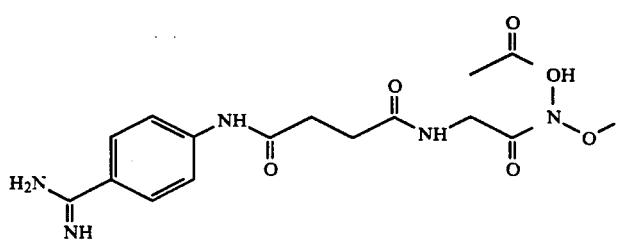

Step 1 Preparation of
3S-amino-4-(methoxymethylamino)4-oxobutanoic acid

To N-tBoc-L-aspartic acid, beta-benzyl ester (10 g, 31 mmole) dissolved in 50 mL methylene chloride was added triethylamine (4.31 mL, 31 mmole). To this was added benzotriazol-1-yloxytris(dimethylamino)phosphonium hexafluorophosphate (BOP)(10.8 g, 31 mmole). After several minutes O,N-dimethylhydroxyl amine hydrochloride (3.40 g, 33.5 mmole) and triethylamine (4.31 mL, 32.3 mmole) was added and the reaction stirred at 25° for several hours. The reaction mixture was diluted to 200 mL by addition of methylene chloride and the reaction mixture was washed successively with dilute aqueous hydrochloric acid, saturated aqueous sodium hydrogen carbonate, and saturated aqueous sodium chloride solution. The organic layer was dried with magnesium sulfate and concentrated in vacuo to give the crude product. This product was dissolved in ethyl acetate and passed over a 4×4 cm pad of Merck 60 silica gel. The ethyl acetate was evaporated to give 8.9 g of desired product (78%).

The N-BOC amido benzyl ester prepared above (7.9 g, 21.6 mmole) was dissolved in 50 mL methanol. The solution was transferred along with 0.5 gm 3% palladium on carbon catalyst to a medium pressure hydrogenation apparatus equipped with a magnetic stirring bar, pressure gauge, and gas inlet and outlet valves. Hydrogen was introduced (54 psig) and the reaction allowed to continue overnight. The catalyst was removed by filtration over a celite pad and the solvent removed in vacuo to give the desired N-BOC amido acid: $^1$H NMR (300 MHz, d$_6$DMSO) δ 1.45 (s, 9H), 2.8 (m, 2H), 3.20 (s, 3H), 3.72 (s, 3H), 4.55 (m, 1H). FABMS 283 (M+ Li).

The N-BOC amido acid prepared above was dissolved in a minimum of 1,4-dioxane and 50 mL of 4N HCl in dioxane added at room temperature. The reaction was allowed to proceed until no further gas evolution was noted (30 minutes) and the solvent evaporated. The desired amino acid as the trifluoroacetate salt was isolated by preparative rphplc and lyophilized to give a white powder (2.33 grams, 8 mmole, 38% overall isolated yield): $^1$H NMR (300 MHz, d$_6$ DMSO) δ 3.02 (bs, 2H), 3.125 (s, 3H), 3.687 (s, 3H), 4.183 (m, 1H). FABMS 177.1 (M+H+).

Step 2 Preparation of 3S-[[4-(aminoiminoethyl)
phenyl]amino]-1,4-dioxobutyl)amino]-4-(methoxymethylamino)4-oxobutanoic acid Coupling of 3S-amino-4-(methoxymethylamino)4-oxobutanoic acid to 4-[[4-(aminoiminomethyl)phenyl]amino]-4-oxobutanoic acid was achieved in a fashion similar to Example 1 Step 2. Thus, 4-[[4-(aminoiminomethyl)phenyl]-amino]-4-oxobutanoic acid hydrochloride (0.70 g, 2.6 mmol) was reacted with isobutylchloroformate (0.34 mL, 2.6 mmol) and an equivalent of N-methylmorpholine (0.29 mL, 2.6 mmole) in DMF. Following activation 3S-amino-4-(methoxymethylamino)4-oxobutanoic acid (0.5 g, 1.7 mmol) was added with an equivalent of N-methylmorpholine and the reaction allowed to proceed overnight. The solvent was removed and the product isolated by preparative hplc and the fractions containing desired product taken to pH 6 with lithium hydroxide. The lithium salt was isolated by lyophilization. $^1$H NMR (300 MHz, d$_6$ DMSO) δ 2.65 (m, 6H), 3.05, 3.10 (s, 3H), 3.65,3.7 (s, 3H), 7.8 (m, 5H), 9.5 (m, 4H), 10.6 (d, 1H). FABMS 394 (M+H), 400.3 (M+Li).

EXAMPLE 45

2S-[[4-[[4-(aminoiminoethyl)phenyl]amino-1,4-dioxobutyl]amino]butanedioic acid

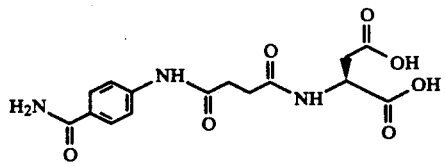

3S-[[4-(aminoiminoethyl)phenyl]amino]-1,4-dioxobutyl]amino]-4-(methoxymethylamino)4-oxobutanoic acid (1.6 g) from Example 11a was taken up in 300 mL water made acidic (pH 2) with trifluoroacetic acid and heated at 60° C. for several hours. The product was isolated by preparative RPHPLC and lyophilized to give desired product (0.84 g). $^1$H NMR (300 MHz, d$_6$ DMSO) Δ 2.55 (bm, 6H), 4.5 (m, 1H), 7.8 (s, 4H), 8.2 (d, 1H), 9.15 (bs, 4H), 10.4 (d, 1H), FABMS 351.3 (M+H).

Elemental Analysis Required for $C_{23}H_{27}N_4O_7 \cdot F_3 \cdot C_2O_2H \cdot H_2O$: C 52.27, H 5.15, N 10.78, Found: C 52.08, H 4.84, N 10.45.

EXAMPLE 46

Ethyl 3-[[4-[[4-(aminoiminomethyl)phenyl]amino]-1,4-dioxobutyl]amino]-2-hydroxy-propanoate

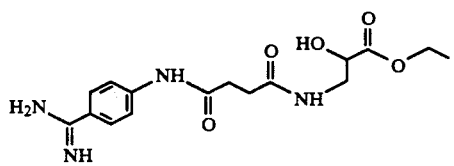

The title compound was prepared in the manner of Example 1 substituting ethyl 3-amino-2-hydroxypropanoate for D,L-3-amino-3-phenylpropionic acid of Example 1 to afford the title compound. The product was verified by $^{13}$C NMR (CD$_3$OD) δ 15.6, 29.1, 31.9, 42.1, 60.8, 69.1, 119.2, 122.2, 128.8, 144.3, 166.3, 172.0, 172.9, 173.6; Fast Atom Bombardment mass spectrometry (MH+)=351.

EXAMPLE 47

Ethyl 3-[[4-[[4-(aminoiminomethyl)phenyl]amino]-1,4-dioxobutyl]amino]-2-methyl-propanoate

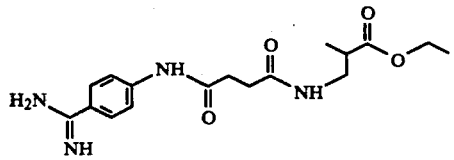

The title compound was prepared in the manner of Example 1 substituting ethyl 3-aminoisobutanoate for D,L-3-amino-3-phenylpropionic acid of Example 1 to afford the title compound. Fast Atom Bombardment mass spectrometry (MH+)=349.

EXAMPLE 48

3-[[4-[[4-(aminoiminomethyl)phenyl]amino]-1,4-dioxobutyl]amino]-2-methyl-propanoic acid

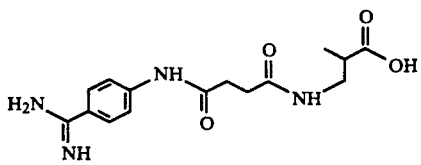

The title compound was prepared by treating the final product of the previous example with porcine liver esterase in the manner of Example 29. The product was purified by reverse phase HPLC using the conditions of Example 1 to afford the title compound. The product was verified by Fast Atom Bombardment mass spectrometry (MH+)=321.

EXAMPLE 49

(±)-3-[[4-[[4-(aminoiminomethyl)phenyl]amino]-1,4-dioxobutyl]amino]-4-phenylsulfonyl butanoic acid

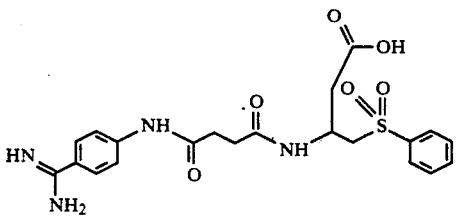

Step 1 Preparation of 3-amino-4-methylsulfonyl butanoic acid

Thiophenol (5 g, 45 mmol) was added to K2CO3 (9.4 g, 67.5 mmol) in dry DMF (100 ml). To this mixture was added methyl 4-chloroacetoacetate (6.8 g, 45 mmol). The progress of the reaction was monitored by tlc (ethylacetate/hexane 30%). After complete reaction (~3 h) 10% aq. HCl was added and the ketoester was extracted into ether to leave 10 g of an amber oil. The crude ketoester was dissolved in methanol (200 ml). To this solution ammonium formate (28 g, 670 mmol) was added followed by NaCNBH3 (2.8 g, 67 mmol) and the solution was stirred for 24 h. The methanol was removed under reduced pressure to leave a solid mass which was added methylene chloride. The excess ammonium formate was removed and filtrate concentrated to leave crude the 3-amino ester. The amino ester was extracted into 10% aq. HCl and extract with ether. The ether extracts were discarded and the aq. layer made basic with aq. NaOH. The product purified by reverse phase chromatography (water/acetonitrile) to result in 3.5 g of a white solid: 1H NMR (d6-DMSO) δ 2.7 (2H), 3.2 (2H), 3.5 (m, 1H), 7.33 (m, 5H), 8.02 (bs, 2H).

Step 2 Preparation of(±)-3-[[4-[[4-(aminoiminomethyl) phenyl]-amino]-1,4-dioxobutyl]amino]-4-phenylsulfonyl butanoic acid 4-[[4-(aminoiminomethyl)phenyl]-amino]-4-oxobutanoic acid hydrochloride prepared in Example 1, Step 1(3.0 g, 11.3 mmol) was added to dry DMF (200 ml) followed by N-methylmorpholine (1.2 g, 11.3 mmol) and isobutyl chloroformate (1.5 g, 17 mmol) at 25° C. The mixture was stirred for 5 min. 3-Amino-4-phenylsulfonyl butanoic acid (4.0 g, 11.3 mmol) was added followed by triethylamine (2.7 g,) and dimethylaminopyridine. After 1 hr the solvent was removed under reduced pressure and the solid mass was dissolved into a mixture of acetic acid:H20:H202 30% (2:2:1) and stirred at 25° C. for 48 hr. The reaction mixture was concentrated in vacuo and the residue purified by reverse phase chromatography (water-/acetonitrile) to result in 3.5 g of a white solid: 1H NMR (d6-DMSO) 2.25 (m, 2H), 2.53 (m, 4H), 3.55 (m, 2H), 4.33 (m, 1H), 7.44 (m, 5H), 7.79 (s, 4H), 7.99 (d, 1H,J=8.1 Hz), 9.1 (bs, 2H), 9.19 (bs, 2H), 10.42 (s, 1H); MS (FAB) m/e 461.2 (MH+H+).

Elemental Analysis Required for C21H24N4O68.F3.C2O2H.H2O C 46.27, H 4.64, N 9.38. Found: C 46.01, H 4.21, N 9.12.

EXAMPLE 50

(±)-Ethyl-3-[[4-[[4-(aminoiminomethyl)phenyl]amino]-1,4-dioxobutyl]amino]-4-phenylsulfonyl butanoate

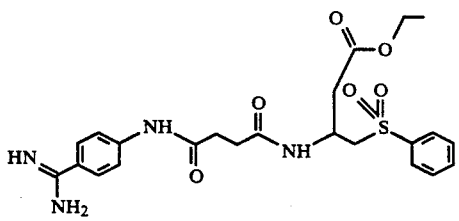

(±)-Ethyl-3-[[4-[[4-(aminoiminomethyl)phenyl]amino]-1,4-dioxobutyl]amino]-4-phenylsulfonyl butanoic acid (1.2 g) from Example IA was suspended in dry ethanol (40 ml) added was 4N HCl in dioxane (20 ml). The progress of the reaction was monitored by RPHPLC. After 2 hours the solvent was removed by rotary evaporator to leave a white solid which was purified by reverse phase chromatography (water-/acetonitrile) to result in 1.1 g of a white solid: 1H NMR (d6-DMSO) δ 1.1 (t, 3H, J=7.5 Hz), 2.25 (m, 2H), 2.53 (m, 4H), 3.55 (m, 2H), 4.0 (q, 2H), J=7.5 Hz) 4.33 (m, 1H), 7.44 (m, 5H), 7.79 (s, 4H), 7.99 (d, 1H,J=8.09 Hz), 9.1 (bs, 2H), 9.19 (bs, 2H), 10.42 (s, 1H); MS (FAB) m/e 489.3 (M+H+).

Elemental Analysis Required for C23H28N4O6S.F3.C2O2H.H2O: C 48.38, H 5.03, N 9.03. Found: C 48.72, H 4.74, N 9.03.

EXAMPLE 51

3-[[4-[[4-(aminoiminomethyl)phenyl](phenylmethyl)-amino]-1,4-dioxobutyl]amino-butyl]amino]-4-pentenoic acid

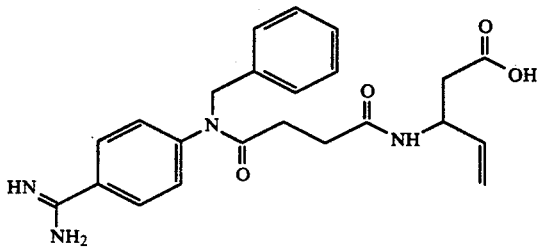

The ethyl ester of the title compound was prepared in the manner of Example 1 substituting 4-[[4-(aminoiminomethyl)phenyl](phenylmethyl)-amino]-4- oxobutanoic acid hydrochloride for 4-[[4-(aminoiminomethyl)-phenyl]amino]- 4-oxobutanoic acid hydrochloride. The ethyl ester was cleaved by treatment with porcine liver esterase in the manner of Example 29. The product was purified by reverse phase HPLC using the conditions of Example 1 to afford the title compound. The product was verified by $^{13}$C NMR (CD$_3$OD) δ 29.4, 30.5, 38.6, 52.4, 114.3, 127.2, 128.0, 128.2, 129.0, 129.0, 136.7, 136.9, 147.0, 166.1, 172.2, 172.3, 172.8; Chemical Ionization Mass Spectrometry (MH+)=423.

Anal. Calcd. for C$_{23}$H$_{26}$N$_4$O$_4$.1.0 CF$_3$CO$_2$H.2.0 H$_2$O: C 52.45, H 5.46, N 9.79, Found: C 52.53, H 5.25, N 9.60.

EXAMPLE 52

Ethyl 13-[[4-[[4-(aminoiminomethyl)naphthyl](phenylmethyl)-amino]-1,4-dioxobutyl]amino]-4-pentenoate

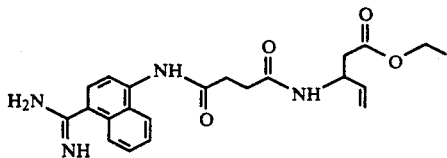

The title compound was prepared in the manner of Example 1 substituting 4-[[4-(aminoiminomethyl)naphthyl]amino]-4-oxobutanoic acid hydrochloride for 4-[[4-(aminoiminomethyl)-3-phenyl]amino]-4-oxobutanoic acid hydrochloride and using ethyl 3-amino-4-pentenoate. The product was purified by reverse phase HPLC using the conditions of Example 1 to afford the title compound. The product was verified by $_{13}$C NMR (CD$_3$OD) δ 13.2, 30.5, 31.3, 39.0, 48.5, 60.4, 114.6, 120.3, 123.1, 123.9, 124.8, 126.6, 127.0, 128.0, 128.1, 130.3, 136.8, 137.4, 167.6, 171.0, 172.6, 173.0; Chemical Ionization Mass Spectrometry (MH+)=411.

Anal. Calcd. for C$_{22}$H$_{26}$N$_4$O$_4$.1.25 CF$_3$CO$_2$H: C 53.21, H 4.97, N 10.13. Found: C 53.23, H 5.01, N 10.24.

EXAMPLE 53

3-[[4-[[4-(aminoiminomethyl)naphthyl)(phenylmethyl))amino]-1,4-dioxobutyl]amino]-4-pentenoic acid

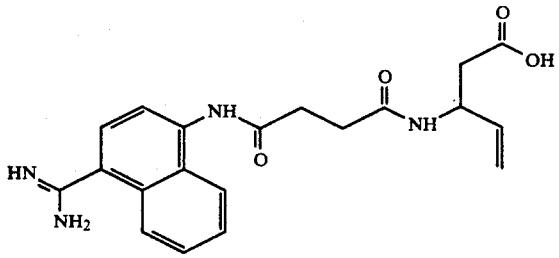

The title compound was prepared by treating the final product of the previous example with porcine liver esterase in the manner of Example 29. The product was purified by reverse phase HPLC using the conditions of Example 1 to afford the title compound. The product was verified by $_{13}$C NMR (CD$_3$OD) δ 30.4, 31.2, 38.6, 48.2, 114.3, 120.3, 123.0, 123.8, 126.5, 126.9, 127.9, 128.0, 130.2, 136.8, 137.3, 167.5, 172.5, 172.8, 172.9; Fast Atom Bombardment Mass Spectrometry (MH+)=383.

Anal Calcd for C$_{20}$H$_{22}$N$_4$O$_4$.1.25 CF$_3$CO$_2$H: C 51.48, H 4.46, N 10.67. Found: C 51.05, H 4.41, N 10.66.

EXAMPLE 54

Ethyl 3-[[4-[[4-(aminoiminomethyl)-2-ethylphenyl]amino]-1,4-dioxobutyl]amino]-4-pentenoate

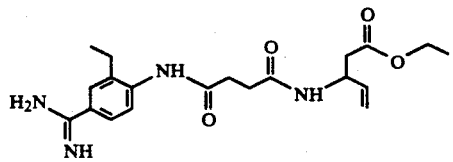

The title compound was prepared in the manner of Example 1 substituting 4-[[4-(aminoiminomethyl)-2-ethylphenyl]amino]-4-oxobutanoic acid hydrochloride for 4-[[4-(aminoiminomethyl)phenyl]amino]-4-oxobutanoic acid hydrochloride and using ethyl 3-amino-4-pentenoate. The product was purified by reverse phase HPLC using the conditions of Example 1 to afford the title compound. The product was verified by $_{13}$C NMR (CD$_3$OD) δ 12.8, 13.1, 23.7, 30.5, 31.3, 38.9, 48.4, 60.4, 114.5, 124.6, 125.2, 125.6, 128.1, 136.8, 138.0, 140.9, 166.8, 171.0, 171.1, 172.5; Chemical Ionization Mass Spectrometry (MH+)=389.

Anal Calcd for C$_{20}$H$_{28}$N$_4$O$_4$.1.0 CF$_3$CO$_2$H.0.25 H$_2$O: C 52.12, H 5.86, N 11.04. Found: C 52.04, H 6.15, N 11.15.

EXAMPLE 55

3-[[4-[[4-(aminoiminomethyl)-2-ethylphenyl]amino]-1,4-dioxobutyl]amino]-4-pentenoic acid

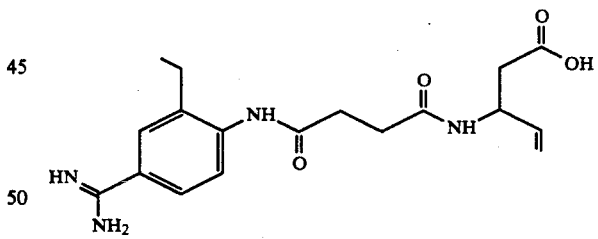

The title compound was prepared by treating the final product of the Example 54 with porcine liver esterase in the manner of Example 29. The product was purified by reverse phase HPLC using the conditions of Example 1 to afford the title compound. The product was verified by $_{13}$C NMR (CD$_3$OD) δ 11.9, 22.9, 29.6, 30.4, 37.8, 47.3, 113.5, 123.6, 124.4, 124.7, 127.3, 136.0, 137.4, 140.1, 166.5, 171.7, 171.8, 172.5; Chemical Ionization Mass Spectrometry (MH+)=361.

Anal Calcd for C$_{18}$H$_{24}$N$_4$O$_4$.1.25 CF$_3$CO$_2$H.0.25 H$_2$O: C 48.52, H 5.11, N 11.04, Found: C 48.31, H 5.04, N 10.95.

EXAMPLE 56

2-[1-[[4-[[4-(aminoiminomethyl)phenyl]-amino]-1,4-dioxybutyl]amino]-ethyl]succinic acid

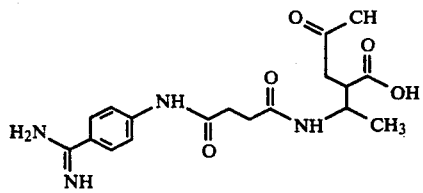

Dimethyl-3-[[4-[[4-(aminoiminomethyl)phenyl]amino]-1,4-dioxobutyl]amino-butyl]amino]-2-(aminoethyl) succinate prepared in Example 15a, Step 1 (600 mg) was added to water/acetonitrile (20 ml) followed by lithium hydroxide (150 mg) at 25° C. The mixture was stirred for 30 min. The course of the reaction was monitored by RPHPLC. After satisfactory product was formed the reaction was neutralized with TFA and purified by reverse phase chromatography (water-/acetonitrile) to result in 250 mg of a white solid: $^1$H NMR (d$_6$-DMSO) δ 0.99 (d, 3H, J=7.1 Hz), 2.44 (m, 2H), 2.55 (m, 4H), 3.14 (m, 1H), 4.15 (m, 1H), 7.78 (s, 4H), 7.92 (d, 1H, J=7.65 Hz), 8.84 (bs, 2H), 9.16 (bs, 2H), 10.25 (s, 1H); MS (FAB) m/e 379.1 (M+H+)

Elemental Analysis Required for $C_{17}H_{22}N_4O_6.F_3.C_2O_2H.H_2O$: C 43.18, H 5.11, N 10.60. Found: C 43.25, H 4.62, N 10.17.

EXAMPLE 57

The following is a prophetical example.

ethyl 3=[[2[[[4(aminoimniomethyl) phenyl]amino[-1-oxo]cyclopropyl]-2-oxo]amino]-4-pentynoate

Step 1. Preparation of ethyl [2-[[[4-(aminoiminomethyl)phenyl]amino]-1-oxo]cyclopropyl] carboxylate.

Diethyl 1,2-cyclopropanedicarboxylate (25 g; trans isomer from Aldrich) is added to a solution of 5.65 g liOH in 50 mL H20. The two phase mixture is stirred and 50 mL ethanol added. After 5 min stirring, a yellow homogeneous mixture is observed and stirring continued for 24 h at 25° C. The crude reaction mixture is partitioned between ethyl acetate and water (pH=9). The ethyl acetate extract should contain 15 g of a mixture 2:1 of monoethyl ester : diacid. A portion of this mixture (7.5 g) is suspended in dichloromethane and treated with a total of 67 mL oxalyl chloride at room temperature for a total time of 20 h. After concentration in vacuo, the residual oil is taken up in 20 mL dimethylformamide and a mixture of aminobenamidine hydrochloride (12.5 g, 0.06 mol) and 15 mL of triethylamine in 50 mL dimethylformamide is slowly added. After 16 hr stirring at 25° C., the reaction is concentrated and the residue taken up in H20/acetonitrile and purified by HPLC. The major peak (detection at 225 nM) is collected (Rt on a linear H20:ACN 5:95→70:30 over 25 min is 16 min). Lyophilization should give about 730 mg of a white powder which should give M+H at 276.2 (calculated for C14H17N3O3:275.1).

Step 2. Preparation of 2-[[[4-(aminoiminomethyl)phenyl]-amino]-1-oxo]cyclopropylcarboxylic acid The product prepared above is stirred in a solution of 1 g LiOH, 5 mL acetonitrile and 10 mL H20 for 6 h. at room temperature. A precipitate should appear upon adjusting the pH to 6 and upon concentration. The precipitate is collected, redissolved in H20.acetonitrile and pH brought to 2 with HCl. This solution after lyophilization should give about 480 mg of white solid: $^1$H NMR (CD$_3$OD) δ 1.3 (m,2H), 1.95 (m, 1H), 2.12 (m, 1H), 7.6 (m, 4H).

Step 3 ethyl 3-[[2[[[[4(aminoiminomethyl) phenyl]amino]-1-oxo]cyclopropyl]-2-oxo]amino]-4-pentynoate The title compound is prepared in the manner of example 1 substituting ethyl 3-amino-4-pentynoate for D-L-3-amino-3-phenylpropionic acid and 2-[[[4-(aminoiminomethyl)phenyl]aminol-oxo]cyclopropylcarboxylic acid hydrochloride for 4-[[4-(aminoiminomethyl)phenyl]-amino-4-oxobutanoic acid hydrochloride. The product is verified by C NMR.

This invention also relates to novel intermediate compounds formed when preparing the above described compounds which is represented by the chemical formula

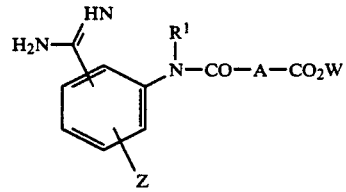

wherein

R$^1$ is selected from hydrogen, lower alkyl radicals, lower alkenyl radicals, aromatic hydrocarbon radicals, alicyclic hydrocarbon radicals, benzyl radicals, phenethyl radicals, where in all of said radicals are optionally substituted with halogen, lower alkoxy, hydroxy and lower alkyl;

A is selected from the group consisting of lower alkyl radicals, lower alkenyl radicals, lower alkynyl radicals, and alicyclic radicals;

Z is selected from the group consisting of hydrogen, lower alkyl, halogen, alkoxy, cyano, sulfonyl, carboxyl, and hydroxyl radicals.

W is as defined above but is preferably hydrogen or lower alkyl. Examples of these intermediates are described in Example 1, Step 1 and Example 2, Step 7 and Example 42, Step 1 and Example 51.

R$^1$ is preferably hydrogen. A is preferably lower alkyl. Z is preferably hydrogen.

In-Vitro Platelet Aggregation in PRP

Healthy male or female dogs were fasted for 8 hours prior to drawing blood; then 30 ml whole blood was collected using a butterfly needle and 30 cc plastic syringe with 3 ml of 0.129 M buffered sodium citrate (3.8%). The syringe was rotated carefully as blood was drawn to mix the citrate. Platelet-rich plasma (PRP) was prepared by centrifugation at 975×g for 3.17 minutes at room temperature allowing the centrifuge to coast to a stop without braking. The PRP was removed from the blood with a plastic pipette and placed in a plastic capped, 50 mL Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×10$^8$ platelets per mL. 400 uL of the PRP preparation and 50 uL of the compounds solution to be tested or saline were preincubated for 1 minute at 37° C. in a BioData, Horsham, Pa.). 50 uL of adenosine 5'diphosphate (ADP) (50 um final concentration) was added to the cuvettes and the aggregation was monitored for 1 minute. All compounds are tested in duplicate. Results are calculated as follows: Percent of control=[(maximal OD minus initial OD of compound) divided by (maximal OD minus initial OD of control saline)]×100. The % inhibition=100−(percent of control).

The compounds tested and their median inhibitory concentrations (IC$_{50}$) are recorded in Table I. IC$_{50}$'s (dosage at which 50% of platelet aggregation is inhibited) were calculated by linear regression of the dose response curve. The assay results for the compounds of Examples 1 to 12 are set forth in Table I, below.

TABLE I

| Example | Dog PRP IC$_{50}$ uM | Ex Vivo Effect after IG Admins. |
|---|---|---|
| 1 | 0.200 | NT |
| 2 | 3.2 | NT |
| 3 | 0.17 | NT |
| 4 | >10 | + |
| 5 | >10 | + |
| 6 | 0.7 | NT |
| 7 | NT | + |
| 8 | >10 | NT |
| 9 | >10 | NT |
| 10 | 0.21 | NT |
| 11 | 1.1 | NT |
| 12 | 5.2 | NT |
| 13 | >10 | + |
| 14 | 0.7 | NT |
| 15 | 1.3 | NT |
| 16 | 0.39 | NT |
| 17 | >10 | + |
| 18 | 0.58 | NT |
| 20 | NT | NT |
| 21 | >10 | NT |
| 22 | NT | NT |
| 23 | NT | NT |
| 24 | NT | NT |
| 25 | NT | NT |
| 26 | NT | NT |
| 27 | NT | NT |
| 28 | NT | NT |
| 29 | 1.5 | NT |
| 30 | NT | NT |
| 31 | 1.5 | NT |
| 32 | >10 | + |
| 33 | 0.27 | NT |
| 34 | >10 | + |
| 35 | 0.36 | NT |
| 36 | NT | NT |
| 37 | 0.29 | NT |
| 38 | 3.0 | + |
| 39 | 0.15 | NT |
| 40 | NT | NT |
| 41 | NT | NT |
| 42 | NT | NT |
| 43 | 0.52 | NT |
| 44 | NT | NT |
| 45 | NT | NT |
| 46 | NT | NT |
| 47 | NT | NT |
| 48 | NT | NT |
| 49 | NT | NT |
| 50 | 0.053 | NT |

TABLE I-continued

| Example | Dog PRP IC$_{50}$ uM | Ex Vivo Effect after IG Admins. |
|---|---|---|
| 51 | 1.8 | NT |
| 52 | NT | NT |
| 53 | NT | NT |
| 54 | NT | NT |
| 55 | NT | NT |

NT — non tested

INHIBITION OF EX VIVO COLLAGEN INDUCED AGGREGATION BY COMPOUNDS OF THE INVENTION PURPOSE

The purpose of this assay is to determine the effects of antiplatelet compounds on ex vivo collagen induced platelet aggregation when administered either intravenously or orally to dogs.

Pretreatment (control) blood samples are drawn from either conscious or anesthetized dogs (Beagles) and centrifuged to prepare platelet rich plasma (PRP). Aggregatory response to collagen is measured in a aggregometer and used as Control. Compounds are administered, either intragasterically (either by capsule or stomach tube or intravenously). Blood samples are drawn at predetermined intervals after compound administration, PRP prepared and aggregation to collagen determined. Compound inhibition of aggregation is determined by comparing the aggregation response after compound administration to the pretreatment response. The study is continued for a maximum of hours or until the platelet aggregation returns to control levels. (If aggregation is still inhibited after 7 hours, a blood sample is drawn the following morning and tested.) Duration of activity is determined by the length of time platelet aggregation is inhibited after compound administration.

Compounds Example #32 and Example #38 were shown to inhibit platelet aggregation at 100% after 24 hours when administered orally to dogs at a dose of 20 mg/kg.

Compound Example 13 was similarly shown to inhibit platelet aggregation at 100% when administered orally to dog at a dose of 12.5 mg/kg. In addition when given orally at that dose for 10 (ten) consecutive days to dogs, compound Example 13 showed sustained antiaggregation activity.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound with the formula:

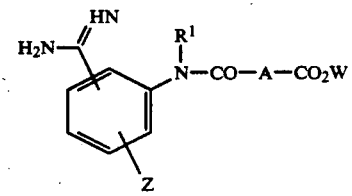

wherein R$^1$ is selected from the group consisting of hydrogen, lower alkyl radicals, lower alkenyl radicals, alicyclic hydrocarbon radicals, aromatic hydrocarbon radicals, benzyl radical and phenethyl radicals;

A is selected from the group consisting of lower alkyl radicals, lower alkenyl radicals, lower alkynyl radicals, and alicyclic radicals;

Z, is selected from the group consisting of hydrogen, lower alkyl, halogen, alkoxy, cyano, sulfonyl, carboxyl, and hydroxyl radicals; and W is hydrogen and lower alkyl.

2. The compound is recited in claim 1, wherein $R^1$ is hydrogen or lower alkyl; A is lower alkyl or alicyclic; Z is hydrogen, alkoxy or sulfonyl; and w is hydrogen.

* * * * *

UNITED STATES PATENT AND TRADEMARK OFFICE
CERTIFICATE OF CORRECTION

PATENT NO. : 5,239,113          Page 1 of 6
DATED : August 24, 1993
INVENTOR(S) : Bovy, et al.

It is certified that error appears in the above-indentified patent and that said Letters Patent is hereby corrected as shown below:

Column 2, line 3, reading "or a n" should read -- or an --.

Column 5, line 26, reading "$Z^1$ is hydrogen" should read -- $Z^1$ is hydrogen. --.

Column 5, line 50, reading "form" should read -- from --.

Column 5, line 61, reading "$R^1$ is hydrogen" should read -- $R^1$ is hydrogen. --.

Column 5, line 63, reading "above" should read -- above. --.

Column 10, line 2, reading "injectable" should read -- injectable formulations --.

Column 11, line 8, reading "120°C." should read -- 120°C. --.

Column 13, line 58, reading "as shown" should read -- as shown in --.

Column 14, line 12, Scheme IV, first structure, reading

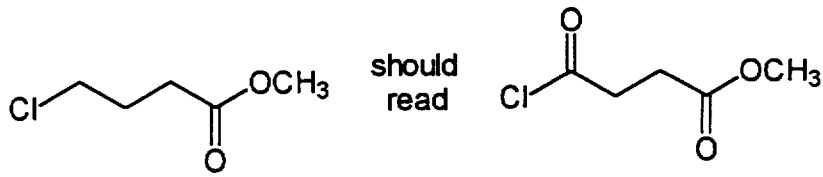

UNITED STATES PATENT AND TRADEMARK OFFICE
CERTIFICATE OF CORRECTION

PATENT NO. : 5,239,113
DATED : August 24, 1993
INVENTOR(S) : Bovy, et al.

It is certified that error appears in the above-indentified patent and that said Letters Patent is hereby corrected as shown below:

Column 14, line 53, Scheme IV, the first part of the last structure, reading

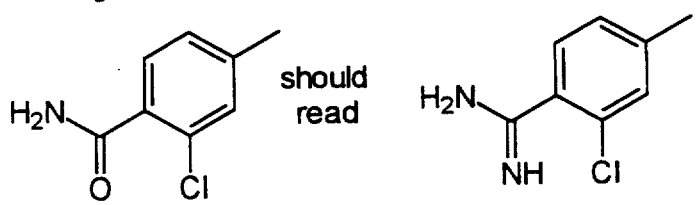

Column 17, line 20, the formula reading

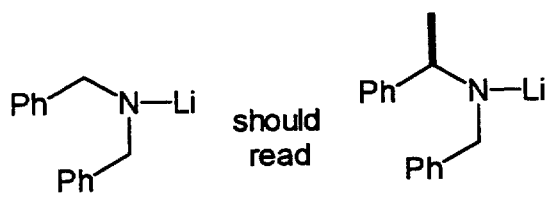

Column 17, line 28, the first part of the formula reading

Column 17, line 61, reading "J. Am. Chem. Soc." should read -- J. Am. Chem. Soc. --

Column 17, line 66, reading "alpa," should read -- alpha, --.

Column 19, line 62, reading "precipitated 20" should read -- precipitated --.

UNITED STATES PATENT AND TRADEMARK OFFICE
CERTIFICATE OF CORRECTION

PATENT NO. : 5,239,113
DATED : August 24, 1993
INVENTOR(S) : Bovy, et al.

Page 3 of 6

It is certified that error appears in the above-indentified patent and that said Letters Patent is hereby corrected as shown below:

Column 20, line 19, reading "1H NMR" should read -- $^1$H NMR --.

Column 20, line 25, reading "$F_3O_2H$." should read -- $F_3C_2O_2H$. --.

Column 22, line 30, reading "$\delta$ 1.2" should read -- $\delta$ 1.2 --.

Column 26, line 44, reading "9.i5" should read -- 9.15 --.

Column 27, line 29, reading "(d, Hz)," should read -- (d, 1H, J = 8.1 Hz), --.

Column 28, line 22, reading "1H NMR" should read -- $^1$H NMR --.

Column 29, line 9, reading "H), 4.05" should read -- 4.05 --.

Column 33, line 36, reading "H); MS" should read -- MS --.

Column 34, line 5, reading ",4-dioxobutyl]" should read -- 1,4-dioxobutyl] --.

Column 34, line 45, reading "1,4dioxobutyl]" should read -- 1,4-dioxobutyl] --.

Column 34, line 66, reading "$H_2O$:" should read --$F_3C_2O_2H.H_2O$--.

Column 36, line 12, reading "$O_5F_3$" should read -- $O_5.F_3$ --.

Column 39, line 30, reading "conditions of" should read -- conditions of Example 1 --.

UNITED STATES PATENT AND TRADEMARK OFFICE
CERTIFICATE OF CORRECTION

PATENT NO. : 5,239,113
DATED : August 24, 1993
INVENTOR(S) : Bovy, et al.

It is certified that error appears in the above-indentified patent and that said Letters Patent is hereby corrected as shown below:

Column 40, line 35, the last part of the formula reading

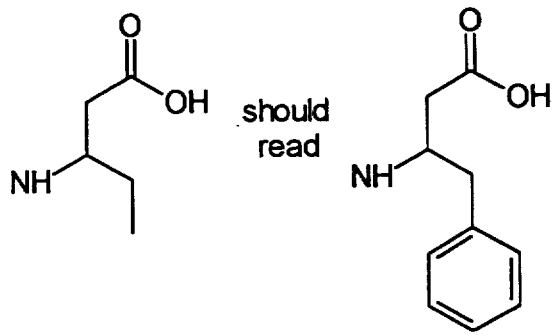

Column 40, line 68, reading "title compound" should read -- title compound. --.

Column 41, line 46, reading "conditions of" should read -- conditions of Example 1 --.

Column 41, line 48, reading "(CD30D)" should read --(CD$_3$OD)--.

Column 41, line 67, reading "title Compound" should read -- title compound --.

Column 42, line 50, the last part of the formula reading

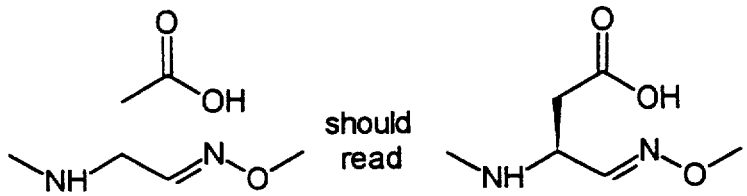

UNITED STATES PATENT AND TRADEMARK OFFICE
CERTIFICATE OF CORRECTION

PATENT NO. : 5,239,113
DATED : August 24, 1993
INVENTOR(S) : Bovy, et al.

It is certified that error appears in the above-indentified patent and that said Letters Patent is hereby corrected as shown below:

Column 42, line 59, reading "example i" should read -- example 1 --.

Column 44, line 42, reading "(CD3OD)" should read --(CD$_3$OD)--.

Column 44, line 65, the formula reading

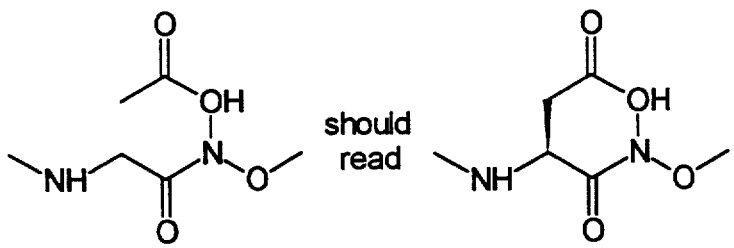

Column 47, line 49, reading "which was" should read -- to which was --.

Column 48, line 13, reading "N$_4$O$_{68}$." should read -- N$_4$O$_6$. --.

Column 48, line 34, reading "Example IA" should read -- Example 1A --.

Column 51, line 37, reading "(aminoimniomethyl)" should read -- (aminoiminomethyl) --.

Column 54, line 31, reading "response The" should read -- response. The --.

UNITED STATES PATENT AND TRADEMARK OFFICE
CERTIFICATE OF CORRECTION

PATENT NO. : 5,239,113

DATED : August 24, 1993

INVENTOR(S) : Bovy, et al.

It is certified that error appears in the above-indentified patent and that said Letters Patent is hereby corrected as shown below:

Column 54, line 32, reading "of hours" should read -- of 24 hours --.

Signed and Sealed this

Nineteenth Day of September, 1995

Attest:

BRUCE LEHMAN

Attesting Officer

Commissioner of Patents and Trademarks